(12) United States Patent
Sukumaran et al.

(10) Patent No.: US 12,408,845 B2
(45) Date of Patent: Sep. 9, 2025

(54) PERSON SUPPORT APPARATUS WITH ADJUSTABLE EXIT DETECTION ZONES

(71) Applicant: Stryker Corporation, Kalamazoo, MI (US)

(72) Inventors: Sujay Sukumaran, Portage, MI (US); Marko N. Kostic, Johnson City, TN (US); Madhu Thomas, London (CA); Krishna Sandeep Bhimavarapu, Kalamazoo, MI (US); Anish Paul, Portage, MI (US); Christopher Alan George, St. Thomas (CA)

(73) Assignee: Stryker Corporation, Kalamazoo, MI (US)

( * ) Notice: Subject to any disclaimer, the term of this patent is extended or adjusted under 35 U.S.C. 154(b) by 1451 days.

(21) Appl. No.: 16/917,004

(22) Filed: Jun. 30, 2020

(65) Prior Publication Data
US 2021/0052197 A1    Feb. 25, 2021

Related U.S. Application Data

(60) Provisional application No. 63/024,066, filed on May 13, 2020, provisional application No. 62/889,254, filed on Aug. 20, 2019.

(51) Int. Cl.
*A61B 5/11*    (2006.01)
*A61B 5/00*    (2006.01)
(Continued)

(52) U.S. Cl.
CPC ............ *A61B 5/1115* (2013.01); *A61B 5/746* (2013.01); *A61G 1/00* (2013.01); *A61G 7/012* (2013.01);
(Continued)

(58) Field of Classification Search
CPC ......... A61B 5/1115; A61B 5/746; A61G 1/00; A61G 7/012; A61G 7/015; A61G 7/018; A61G 7/0507; A47C 19/04
(Continued)

(56) References Cited

U.S. PATENT DOCUMENTS

| RE28,754 E | 3/1976 | Cook et al. |
| 4,175,263 A | 11/1979 | Triplett et al. |

(Continued)

FOREIGN PATENT DOCUMENTS

| AU | 2020204399 A1 * | 3/2021 | ........... A61B 5/1115 |
| CA | 3085085 A1 * | 2/2021 | ........... A61B 5/1115 |

(Continued)

OTHER PUBLICATIONS

Canadian Office Action for Canadian Application No. Application No. 3,085,085, dated Oct. 1, 2024.

*Primary Examiner* — Robert G Santos
(74) *Attorney, Agent, or Firm* — Gardner, Linn, Burkhart & Ondersma LLP

(57) ABSTRACT

A person support apparatus, such as a bed, cot, stretcher, or the like, for a supporting an occupant includes an exit detection system that has, in some embodiments, multiple user-selectable zones. An alert is triggered when the occupant crosses a boundary of the selected zone. A first zone has a boundary that is adjusted based on a condition of the person support apparatus, such as the width of the support deck or other characteristic. A second zone has a boundary that is not adjusted based on the condition of the person support apparatus, but which may have a boundary that is dependent on an initial location of the occupant when the exit detection system is armed. The initial location of the occupant may correspond to a center of gravity of the occupant.

14 Claims, 16 Drawing Sheets

(51) Int. Cl.
*A61G 1/00* (2006.01)
*A61G 7/012* (2006.01)
*A61G 7/015* (2006.01)
*A61G 7/018* (2006.01)
*A61G 7/05* (2006.01)

(52) U.S. Cl.
CPC ............. *A61G 7/015* (2013.01); *A61G 7/018* (2013.01); *A61G 7/0507* (2013.01); *A61G 2203/32* (2013.01); *A61G 2203/44* (2013.01)

(58) Field of Classification Search
USPC ............................ 5/610, 611, 600, 185, 181
See application file for complete search history.

(56) References Cited

U.S. PATENT DOCUMENTS

| | | | |
|---|---|---|---|
| 4,242,672 A | 12/1980 | Gault | |
| 5,802,640 A | 9/1998 | Ferrand et al. | |
| 5,844,488 A | 12/1998 | Musick | |
| 6,009,570 A | 1/2000 | Hargest et al. | |
| 6,049,281 A | 4/2000 | Osterweil | |
| 6,067,019 A | 5/2000 | Scott | |
| 6,208,250 B1 | 3/2001 | Dixon et al. | |
| 6,585,645 B2 | 7/2003 | Hutchinson | |
| 6,754,516 B2 | 6/2004 | Mannheimer | |
| 6,791,460 B2 | 9/2004 | Dixon et al. | |
| 7,253,366 B2 | 8/2007 | Bhai | |
| 7,304,580 B2 | 12/2007 | Sullivan et al. | |
| 7,369,680 B2 | 5/2008 | Trajkovic et al. | |
| 7,437,787 B2 | 10/2008 | Bhai | |
| 7,502,498 B2 | 3/2009 | Wen et al. | |
| 7,538,659 B2 | 5/2009 | Ulrich et al. | |
| 7,541,934 B2 | 6/2009 | Fredriksson et al. | |
| 7,612,666 B2 | 11/2009 | Badawy | |
| 7,629,890 B2 | 12/2009 | Sullivan et al. | |
| 7,656,299 B2 | 2/2010 | Gentry et al. | |
| 7,666,151 B2 | 2/2010 | Sullivan et al. | |
| 7,714,728 B2 | 5/2010 | Koblasz | |
| 7,834,770 B2 | 11/2010 | Kazuno | |
| 7,987,069 B2 | 7/2011 | Rodgers et al. | |
| 8,042,206 B2 | 10/2011 | Genaro | |
| 8,082,160 B2 | 12/2011 | Collins, Jr. et al. | |
| 8,258,963 B2 | 9/2012 | Dixon et al. | |
| 8,266,742 B2 | 9/2012 | Andrienko | |
| 8,272,087 B2 | 9/2012 | Westermann | |
| 8,281,433 B2 | 10/2012 | Riley et al. | |
| 8,284,047 B2 | 10/2012 | Collins, Jr. et al. | |
| 8,381,336 B2 | 2/2013 | Kazuno et al. | |
| 8,525,680 B2 | 9/2013 | Riley et al. | |
| 8,723,677 B1 | 5/2014 | Kiani | |
| 8,756,078 B2 | 6/2014 | Collins, Jr. et al. | |
| 8,821,418 B2 | 9/2014 | Meger et al. | |
| 8,830,070 B2 | 9/2014 | Dixon et al. | |
| 8,838,411 B2 | 9/2014 | Kazuno et al. | |
| 8,844,073 B2 | 9/2014 | Riley et al. | |
| 8,902,066 B2 | 12/2014 | Parker et al. | |
| 8,907,287 B2 | 12/2014 | Vanderpohl | |
| 9,013,313 B2 | 4/2015 | Paine | |
| 9,044,367 B2 | 6/2015 | Yakam et al. | |
| 9,138,173 B2 | 9/2015 | Penninger et al. | |
| 9,177,465 B2 | 11/2015 | Vanderpohl, III | |
| 9,179,863 B2 | 11/2015 | Brauers et al. | |
| 9,198,815 B2 | 12/2015 | Murai | |
| 9,226,696 B2 | 1/2016 | Kiani | |
| 9,253,891 B2 | 2/2016 | Williams | |
| 9,295,600 B2 | 3/2016 | Receveur | |
| 9,320,444 B2 | 4/2016 | Hayes et al. | |
| 9,378,632 B2 | 6/2016 | Venetianer et al. | |
| 9,445,751 B2 | 9/2016 | Young et al. | |
| 9,489,818 B2 | 11/2016 | Vanderpohl, III | |
| 9,504,619 B2 | 11/2016 | Murai | |
| 9,539,156 B2 | 1/2017 | Lemire et al. | |
| 9,549,675 B2 | 1/2017 | Riley et al. | |
| 9,579,047 B2 | 2/2017 | Clark et al. | |
| 9,727,061 B2 | 8/2017 | Liu et al. | |
| 9,750,654 B2 | 9/2017 | Brondum | |
| 9,754,476 B2 | 9/2017 | Lemire et al. | |
| 9,775,758 B2 | 10/2017 | Riley et al. | |
| 9,782,108 B2 | 10/2017 | Shimizu | |
| 9,795,321 B2 | 10/2017 | Shimizu | |
| 9,814,410 B2 | 11/2017 | Kostic et al. | |
| 9,861,321 B2 | 1/2018 | Collins, Jr. et al. | |
| 9,875,633 B2 | 1/2018 | Pirio et al. | |
| 9,883,809 B2 | 2/2018 | Klap et al. | |
| 10,357,185 B2* | 7/2019 | Kostic | A61B 5/6892 |
| 10,617,327 B2* | 4/2020 | Kostic | A61G 7/0524 |
| 10,786,408 B2* | 9/2020 | Sidhu | A61G 7/018 |
| 11,490,834 B2* | 11/2022 | Sukumaran | G08B 29/185 |
| 11,800,995 B2* | 10/2023 | Sukumaran | A61G 7/0509 |
| 12,036,161 B2* | 7/2024 | Connell | A61G 7/0524 |
| 12,144,607 B2* | 11/2024 | Kostic | A61G 7/018 |
| 12,268,642 B2* | 4/2025 | Sidhu | A61B 5/1115 |
| 2003/0018241 A1 | 1/2003 | Mannheimer | |
| 2007/0038155 A1 | 2/2007 | Kelly, Jr. et al. | |
| 2009/0044334 A1 | 2/2009 | Parsell et al. | |
| 2011/0068932 A1 | 3/2011 | Flocard et al. | |
| 2011/0153915 A1 | 6/2011 | Zitlaw | |
| 2012/0075464 A1 | 3/2012 | Derenne et al. | |
| 2014/0115784 A1 | 5/2014 | Johannigman et al. | |
| 2014/0313030 A1 | 10/2014 | Ten Kate et al. | |
| 2014/0343889 A1 | 11/2014 | Ben Shalom et al. | |
| 2015/0108443 A1 | 4/2015 | Huh et al. | |
| 2015/0238123 A1 | 8/2015 | Yakam et al. | |
| 2015/0323388 A1 | 11/2015 | Kostic et al. | |
| 2015/0327777 A1 | 11/2015 | Kostic et al. | |
| 2016/0022218 A1 | 1/2016 | Hayes et al. | |
| 2016/0023144 A1 | 1/2016 | Fitzgerald et al. | |
| 2016/0106345 A1 | 4/2016 | Kostic et al. | |
| 2016/0128610 A1 | 5/2016 | Kostic et al. | |
| 2016/0140307 A1 | 5/2016 | Brosnan et al. | |
| 2016/0140827 A1 | 5/2016 | Derenne et al. | |
| 2016/0193095 A1 | 7/2016 | Roussy et al. | |
| 2017/0042750 A1 | 2/2017 | Murai | |
| 2017/0098359 A1 | 4/2017 | Sidhu et al. | |
| 2017/0143566 A1 | 5/2017 | Elku et al. | |
| 2017/0156638 A1 | 6/2017 | Ribble et al. | |
| 2017/0224253 A1 | 8/2017 | Berlin et al. | |
| 2017/0243459 A9* | 8/2017 | Sidhu | A61G 7/005 |
| 2018/0108239 A1 | 4/2018 | Pirio et al. | |
| 2020/0214599 A1* | 7/2020 | Kostic | A61G 7/0524 |
| 2021/0007919 A1* | 1/2021 | Sidhu | A61G 7/005 |
| 2021/0045950 A1* | 2/2021 | Connell | A61G 7/0524 |
| 2021/0052197 A1* | 2/2021 | Sukumaran | A61B 5/6892 |
| 2021/0338505 A1* | 11/2021 | Nahavandi | A61B 5/747 |
| 2021/0353179 A1* | 11/2021 | Sukumaran | A61G 7/0528 |
| 2023/0067526 A1* | 3/2023 | Sukumaran | A61G 7/0509 |
| 2023/0233102 A1* | 7/2023 | Paul | A61B 5/6892 5/611 |
| 2024/0277543 A1* | 8/2024 | Sukumaran | A61G 7/005 |
| 2024/0299226 A1* | 9/2024 | Sukumaran | A61B 5/1115 |
| 2025/0031999 A1* | 1/2025 | Kostic | A61B 5/1115 |

FOREIGN PATENT DOCUMENTS

| | | | | |
|---|---|---|---|---|
| CA | 3171373 A1 * | 11/2021 | | A61B 5/1115 |
| CA | 3181260 A1 * | 4/2022 | | A61B 5/004 |
| CN | 101558011 A | 10/2009 | | |
| EP | 1976433 B1 | 3/2011 | | |
| EP | 2725507 B1 | 10/2013 | | |
| JP | 2013240601 A | 12/2013 | | |
| WO | 9730351 | 8/1997 | | |
| WO | 9834577 A1 | 8/1998 | | |
| WO | 2009029996 A1 | 3/2009 | | |
| WO | 2009055635 A1 | 4/2009 | | |
| WO | 2011113070 A1 | 9/2011 | | |
| WO | 2015136424 A1 | 9/2015 | | |
| WO | 2015167643 A1 | 11/2015 | | |
| WO | WO-2020102129 A1 * | 5/2020 | | A61B 5/1115 |
| WO | WO-2021231674 A1 * | 11/2021 | | A61B 5/1115 |
| WO | WO-2022072340 A1 * | 4/2022 | | A61B 5/0004 |
| WO | WO-2023064182 A1 * | 4/2023 | | A61B 5/115 |
| WO | WO-2023064183 A1 * | 4/2023 | | A61G 7/005 |
| WO | WO-2023064184 A1 * | 4/2023 | | |

(56) References Cited

FOREIGN PATENT DOCUMENTS

| WO | WO-2023225090 A1 | * | 11/2023 | |
|----|------------------|---|---------|---|
| WO | WO-2023225246 A1 | * | 11/2023 | ........... A61B 5/1115 |
| WO | WO-2024039620 A2 | * | 2/2024 | ............. A61G 7/005 |

* cited by examiner

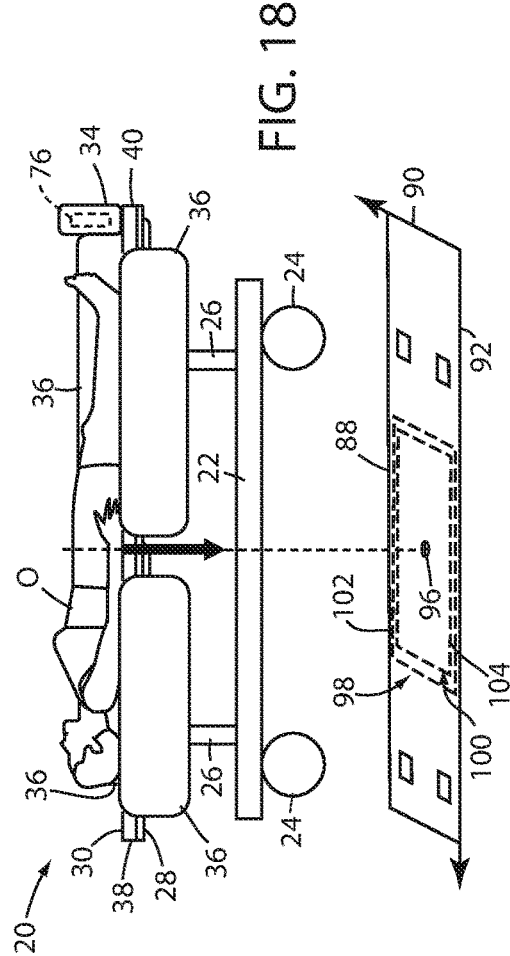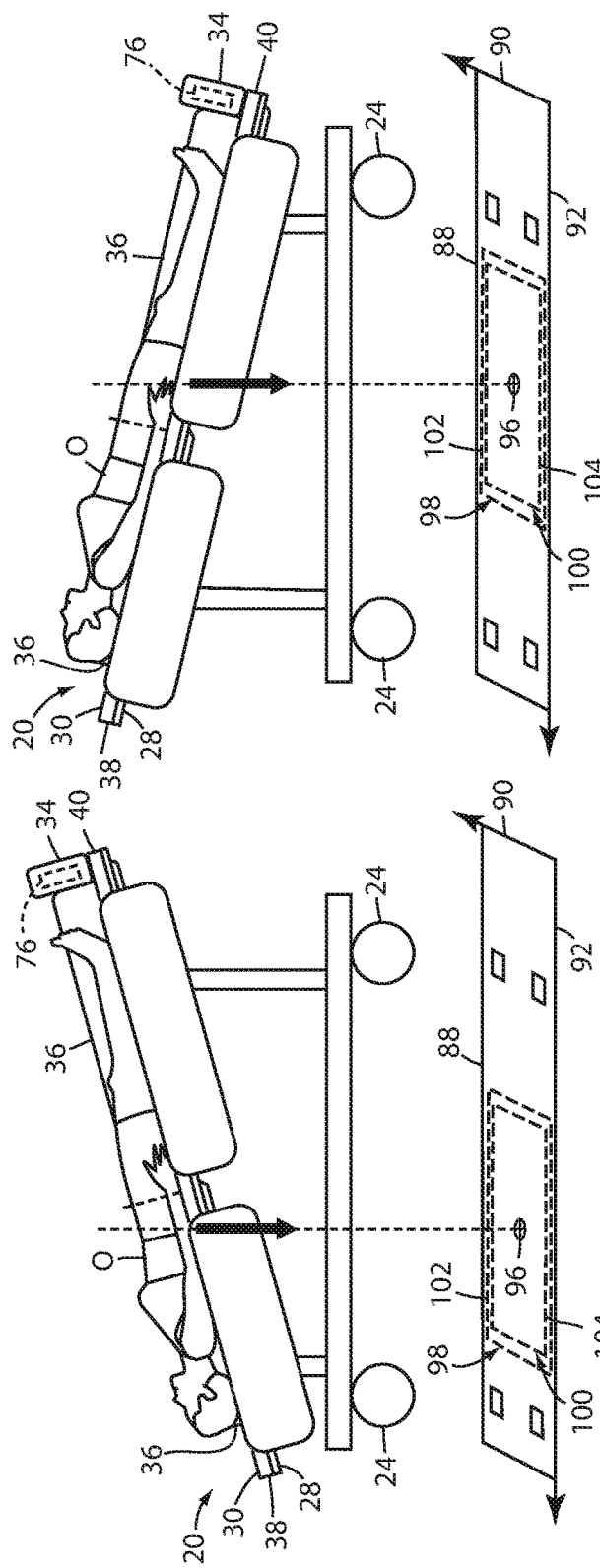

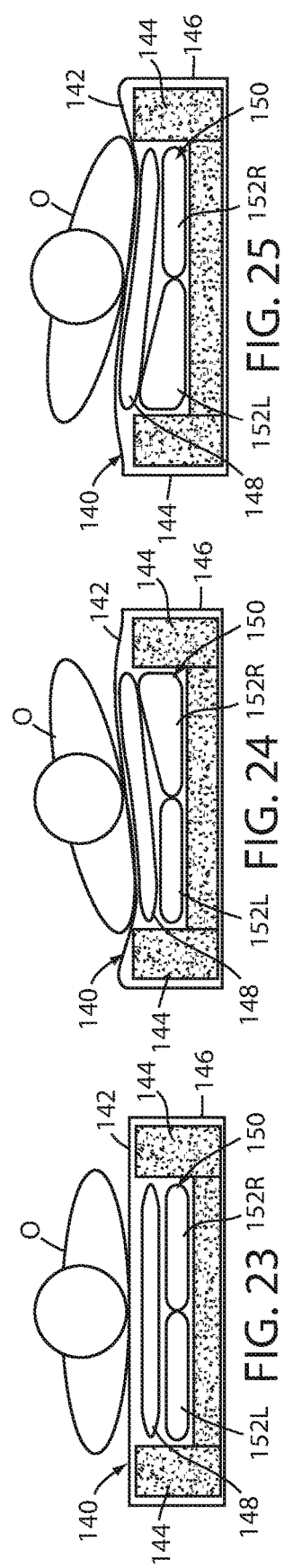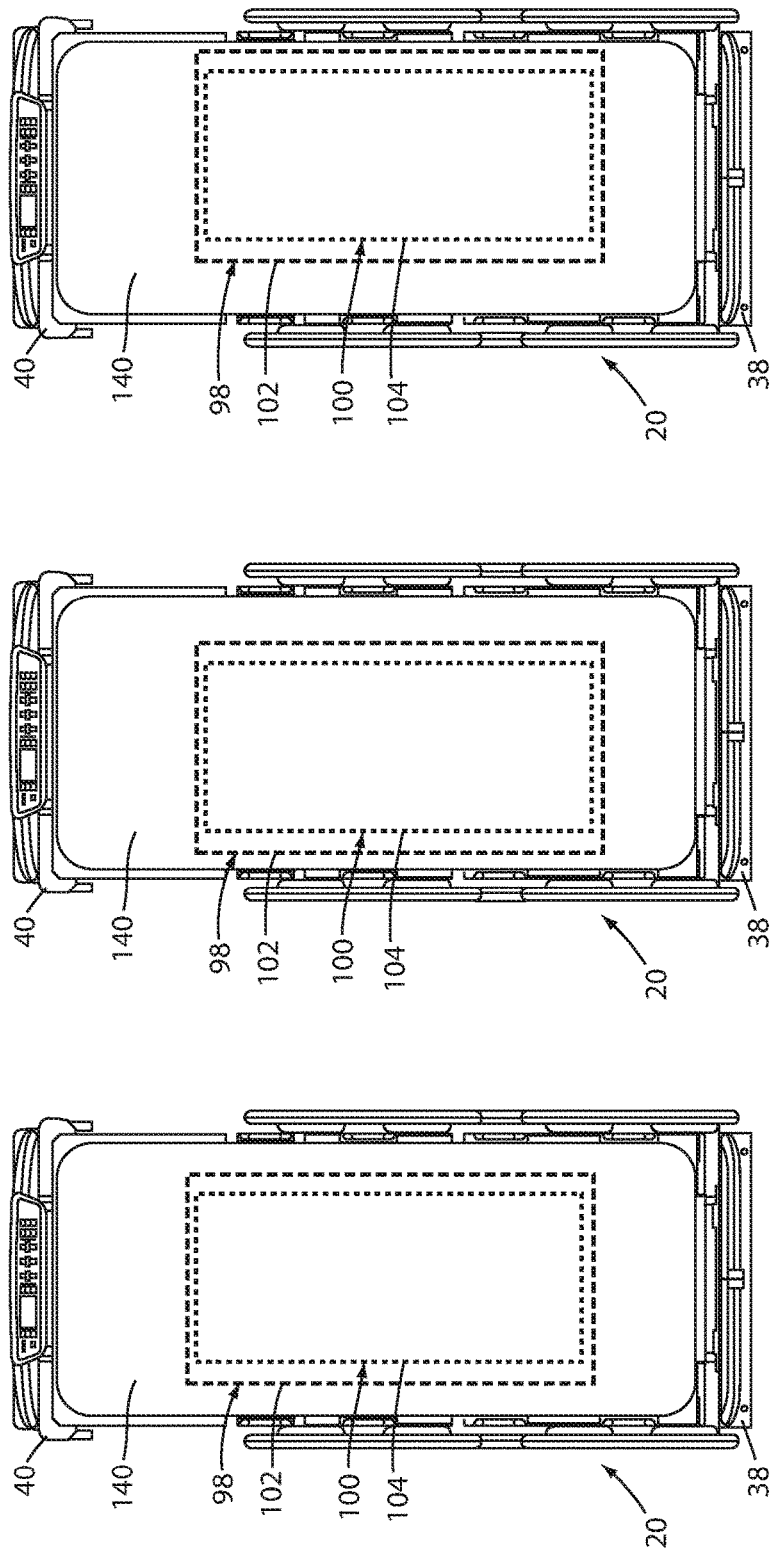

PERSON SUPPORT APPARATUS WITH ADJUSTABLE EXIT DETECTION ZONES

CROSS-REFERENCE TO RELATED APPLICATIONS

This application claims priority to U.S. provisional patent applications 62/889,254 filed Aug. 20, 2019, by inventors Sujay Sukumaran et al. and entitled PERSON SUPPORT APPARATUS WITH ADJUSTABLE EXIT DETECTION ZONES, and to U.S. provisional patent application Ser. No. 63/024,066 filed May 13, 2020, by inventors Grady Sertic et al. and entitled PATIENT SUPPORT APPARATUS WITH AUTOMATIC EXIT DETECTION MODES OF OPERATION, the complete disclosures of both of which are incorporated herein by reference.

BACKGROUND

The present disclosure relates to person support apparatuses, such as beds, cots, stretchers, recliners, or the like. More specifically, the present disclosure relates to person support apparatuses that include sensors for monitoring the motion and/or activity of an occupant of the person support apparatus and issuing an alert if the occupant is about to, or does, exit the person support apparatus.

Existing hospital beds and/or stretchers often include an exit detection system that is adapted to detect when a patient has exited the bed, or when a patient may be about to exit the bed. Typically, such beds include circuitry for providing an audio or visual alert when such an exit or pre-exit situation is detected. In many cases, the bed or stretchers include circuitry for transmitting a signal to a remote location, such as a nurses' station, so that the appropriate caregivers are notified of the exit, or pre-exit condition, and can respond appropriately. The exit detection system itself may be implemented in a variety of manners, including using a plurality of force sensors.

SUMMARY

According to various embodiments, an improved person support apparatus is provided that adjusts a size, shape, position, or other characteristic of one or more alert zones of an exit detection system based on one or more conditions of the person support apparatus. The exit detection system issues an alert if an occupant of the person support apparatus moves outside of whichever one of the alert zones has been designated as the active alert zone. The exit detection system may also include an arming zone for each of the alerting zones. The exit detection system may adjust the boundary of one or more of the arming zones in addition to adjusting the boundary of one or more of the alerting zones. The adjustable alerting zones allow improved alerting regarding an occupant's intention to exit the person support apparatus, including, but not limited to, advance notification of such an exit and a reduction in false alarms. The improved monitoring of the occupant's motion may also provide a reduction in failures to arm the exit detection system.

A person support apparatus according to one embodiment of the present disclosure includes a litter frame, a plurality of lifts adapted to raise and lower the litter frame, a support deck, and an exit detection system. The support deck is supported on the litter frame and configured to have an adjustable width. The exit detection system is adapted to issue an alert if an occupant of the person support apparatus moves outside of a boundary of an alert zone. The exit detection system comprises a plurality of force sensors adapted to output signals corresponding to downward forces exerted on the support deck, and a controller. The controller is in communication with the force sensors and is configured to determine a width of the support deck and adjust the boundary of the alert zone based on the deck width.

A person support apparatus according to another embodiment of the present disclosure includes a litter frame, a plurality of lifts adapted to raise and lower the litter frame, a support deck, an arming control, and an exit detection system. The support deck is supported on the litter frame and configured to have an adjustable width. The exit detection system is adapted to issue an alert if an occupant of the person support apparatus moves outside of an alert zone, and the exit detection system includes an arming zone having a boundary in which the occupant must remain present during an arming process of the exit detection system. The exit detection system comprises a plurality of force sensors adapted to output signals corresponding to downward forces exerted on the support deck, and a controller. The controller communicates with the force sensors and is configured to determine a condition of the person support apparatus; to adjust the boundary of the arming zone based on the condition of the person support apparatus; to arm the exit detection system in response to a user activating the arming control if the occupant remains in the arming zone during the arming process of the exit detection system; and to not arm the exit detection system in response to the user activating the arming control if the occupant does not remain in the arming zone during the arming process of the exit detection system.

A person support apparatus according to another embodiment of the present disclosure includes a litter frame, a plurality of lifts adapted to raise and lower the litter frame, a support deck, and an exit detection system. The exit detection system is adapted to issue an alert if an occupant of the person support apparatus moves outside of a user-selected one of a plurality of alert zones. A first one of the plurality of alert zones has a variable boundary defined independently of a location of the occupant when the exit detection system is initially armed, and a second one of the plurality of alert zones has a static boundary defined by a location of the occupant when the exit detection system is initially armed. The exit detection system comprises a plurality of force sensors adapted to output signals corresponding to downward forces exerted on the support deck, and a controller. The controller communicates with the plurality of force sensors and is configured to determine a condition of the person support apparatus. The controller is further configured, after the exit detection system has been armed, to adjust the variable boundary of the first alert zone, but not the static boundary of the second alert zone, based on the condition of the person support apparatus.

A person support apparatus according to another embodiment of the present disclosure includes a litter frame, a plurality of lifts adapted to raise and lower the litter frame, a support deck, and an exit detection system. The exit detection system is adapted to issue an alert if an occupant of the person support apparatus moves outside of a user-selected one of a plurality of alert zones. The plurality of alert zones includes a first alert zone and a second alert zone. The exit detection system comprises a plurality of force sensors adapted to output signals corresponding to downward forces exerted on the support deck, and a controller. The controller communicates with the plurality of force sensors and is configured to determine a condition of the person support apparatus, to adjust the boundary of the first alert zone based on the condition of the person support apparatus, and to not adjust the boundary of the second alert zone based on the condition of the person support apparatus.

A person support apparatus according to another embodiment of the present disclosure includes a litter frame, a plurality of lifts adapted to raise and lower the litter frame, a support deck, a mattress interface, and an exit detection system. The mattress interface is adapted to receive status data from a mattress configured to provide lateral rotation therapy to an occupant of the person support apparatus. The lateral rotation therapy comprises rotating the occupant laterally in a direction. The exit detection system is adapted to issue an alert if an occupant of the person support apparatus moves outside of a boundary of an alert zone. The exit detection system comprises a plurality of force sensors adapted to output signals corresponding to downward forces exerted on the support deck, and a controller. The controller communicates with the mattress interface and the plurality of force sensors. The controller is configured to receive the status data from the mattress interface, to determine a status of the lateral rotation therapy based on the status data; and to adjust the boundary based on the status of the lateral rotation therapy.

A person support apparatus according to another embodiment of the present disclosure includes a litter frame, a plurality of lifts adapted to raise and lower the litter frame, a support deck, and an exit detection system. The exit detection system is adapted to issue an alert if an occupant of the person support apparatus moves outside of a boundary of an alert zone. The exit detection system comprises a plurality of force sensors adapted to output signals corresponding to downward forces exerted on the support deck, and a controller. The controller communicates with the plurality of force sensors and is configured to determine an incline angle of the litter frame and to adjust the boundary of the alert zone based on the incline angle.

A person support apparatus according to another embodiment of the present disclosure includes a litter frame, a plurality of lifts adapted to raise and lower the litter frame, a support deck, and an exit detection system. The exit detection system is adapted to issue an alert if an occupant of the person support apparatus moves outside of a boundary of an alert zone. The exit detection system comprises a plurality of force sensors adapted to output signals corresponding to downward forces exerted on the support deck, and a controller. The controller communicates with the plurality of force sensors and is configured to detect an addition of a non-occupant object to the support deck or a removal of a non-occupant object from the support deck, and to adjust the boundary based on the addition or removal of the non-occupant object.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 18 is a diagram of the person support apparatus illustrating an alert zone and an arming zone within a reference frame, shown with a litter frame in a horizontal orientation.

FIG. 19 is a diagram of the person support apparatus of FIG. 18 showing a modification of the zones in response to the litter frame moving to a Trendelenburg orientation.

FIG. 20 is a diagram of the person support apparatus of FIG. 18 showing another modification of the zones in response to the litter frame moving to a reverse Trendelenburg orientation.

FIG. 23 is a transverse cross-section of a mattress for the person support apparatus of FIG. 1, the mattress configured to provide lateral rotation therapy to an occupant.

FIG. 24 is a view similar to FIG. 23, illustrating lateral rotation of the occupant to the left by a leftward incline of the mattress.

FIG. 25 is a view similar to FIG. 23, illustrating lateral rotation of the occupant to the right by a rightward incline of the mattress.

FIG. 26 is a plan view diagram of the person support apparatus illustrating an alert zone used to trigger an exit alarm and an arming zone used to arm the exit detection system, when the mattress is in a non-rotated or horizontal orientation as shown in FIG. 23.

FIG. 27 is a plan view diagram of the person support apparatus of FIG. 26 showing a modification of the zones in response to lateral rotation to a leftward incline as shown in FIG. 24.

FIG. 28 is a plan view diagram of the person support apparatus of FIG. 26 showing another modification of the zones in response to lateral rotation to a rightward incline as shown in FIG. 25.

DETAILED DESCRIPTION OF THE EMBODIMENTS

Figure 1:
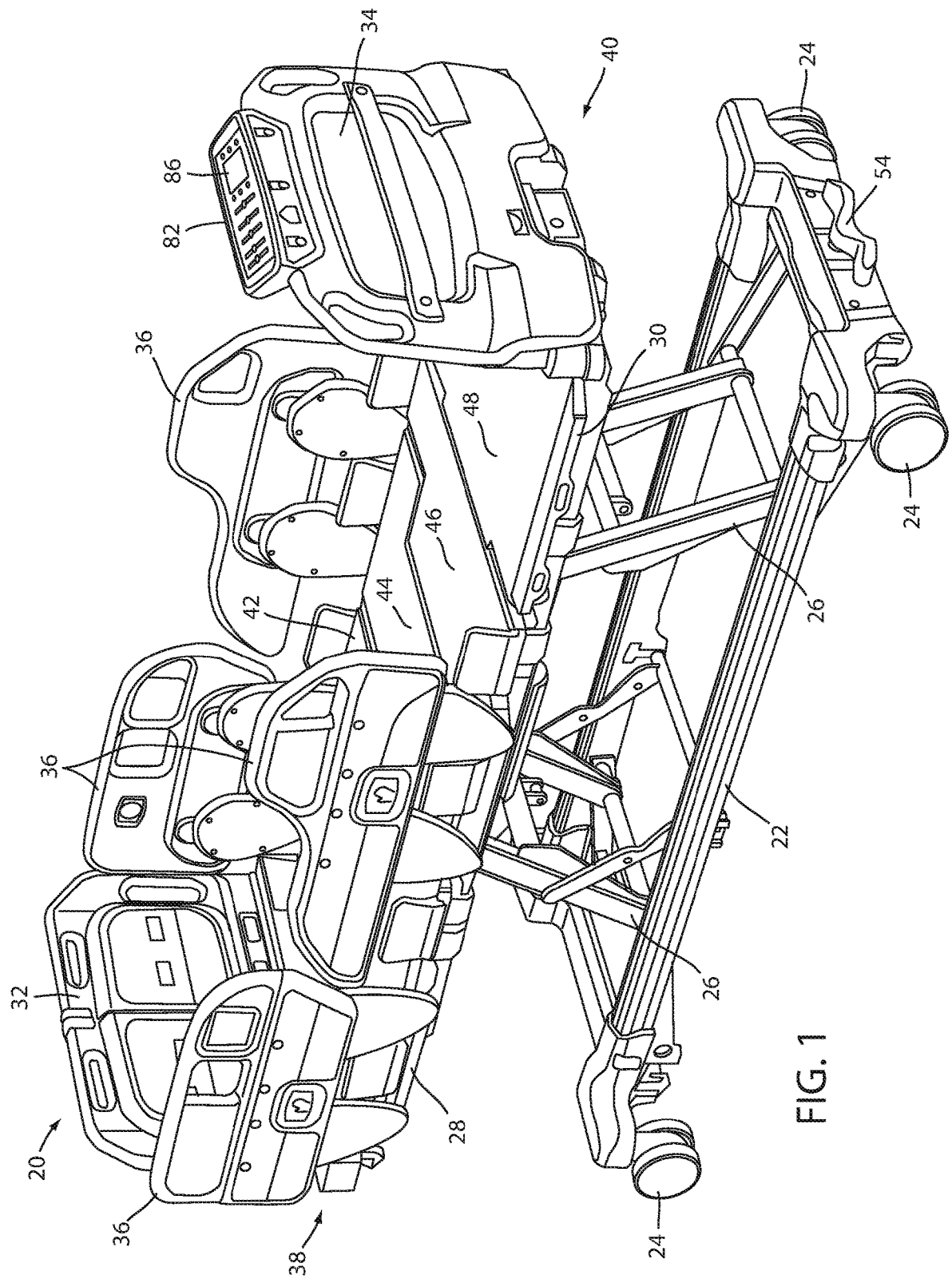
FIG. 1 is a perspective view of a person support apparatus according to one embodiment of the disclosure.

An illustrative person support apparatus 20 that may incorporate one or more aspects of the present disclosure is shown in FIG. 1. Although the particular form of person support apparatus 20 illustrated in FIG. 1 is a bed adapted for use in a hospital or other medical setting, it will be understood that person support apparatus 20 could, in different embodiments, be a cot, a stretcher, a gurney, a recliner, a residential bed, or any other structure capable of supporting a person, whether stationary or mobile and/or whether medical or residential.

In general, person support apparatus 20 includes a base 22 having a plurality of wheels 24, a pair of lifts 26 supported on the base, a litter frame 28 supported on the lifts 26, and a support deck 30 supported on the litter frame 28. Person support apparatus 20 further includes a headboard 32, a footboard 34, and a plurality of siderails 36. Siderails 36 are all shown in a raised position in FIG. 1 but are each individually movable to a lower position in which ingress into, and egress out of, person support apparatus 20 is not obstructed by the lowered siderails 36. In some embodiments, siderails 36 may be moved to one or more intermediate positions as well.

Lifts 26 are adapted to raise and lower litter frame 28 with respect to base 22. Lifts 26 may be hydraulic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted, to place the litter frame 16 in a flat or horizontal orientation, a Trendelenburg orientation, or a reverse Trendelenburg orientation. That is, litter frame 28 includes a head end 38 and a foot end 40, each of whose height can be independently adjusted by the nearest lift 26. Person support apparatus 20 is designed so that when an occupant lies thereon, his or her head will be positioned adjacent head end 38 and his or her feet will be positioned adjacent foot end 40.

Litter frame 28 provides a structure for supporting support deck 30, the headboard 32, footboard 34, and siderails 36. Support deck 30 provides a support surface for a mattress (not shown in FIG. 1), or other soft cushion, so that a person may lie and/or sit thereon. The top surface of the mattress or other cushion forms a support surface for the occupant.

Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (shown in FIG. 1) and a plurality of raised positions (not shown). Thigh section 46 and foot section 48 may also be pivotable about generally horizontal pivot axes.

Figure 2:
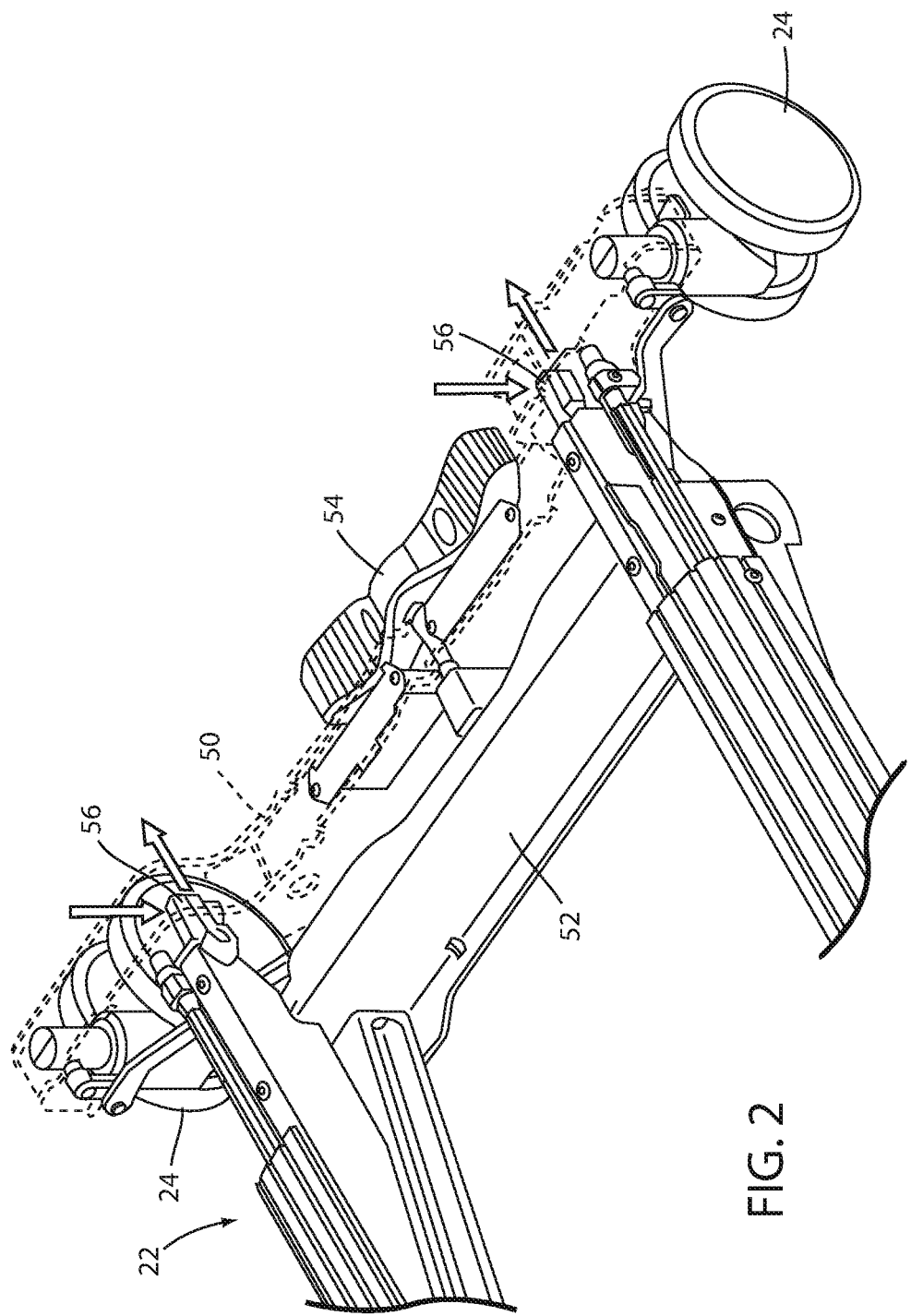
FIG. 2 is a perspective view of a portion of a base of the person support apparatus of FIG. 1, including a plurality of force sensors of an exit detection system.

FIG. 2 illustrates in greater detail a portion of the base 22, including two of the wheels 24. Base 22 includes a wheel frame 50 and a base frame 52 supported by the wheel frame 50. A portion of the wheel frame 50 is shown transparently in FIG. 2 to better illustrate details of the base 22. The wheel frame 50 supports the plurality of wheels 24 proximate the corners of the base frame 52. A brake pedal 54 may permit locking one or more of the wheels 24 in a full stop state or a steered state, in addition to an unlocked state that permits the wheels 24 to both swivel and rotate.

The lower ends of the lifts 26 are connected to the base frame 52. Through this connection, the base frame 52 supports litter frame 28, support deck 30, footboard 34, the headboard, and siderails 36, and other components of the person support apparatus 10.

Base frame 52 includes a plurality of force sensors 56 resting on the wheel frame 50. In the illustrated embodiment, the force sensors 56 are proximate the corners of the base frame 52, with two of four force sensors 56 shown in FIG. 2. The force sensors 56 may be load cells, or other types of force sensors, such as, but not limited to, linear variable displacement transducers and/or any one or more capacitive, inductive, and/or resistive transducers that are configured to produce a changing output in response to changes in the force exerted against them. The force sensor 56 may be electronically connected to control circuitry through an electrical contact (not shown).

Although the illustrated embodiment of person support apparatus 20 includes a total of four force sensors 56, two of which are shown in FIG. 2, it will be understood by those skilled in the art that different numbers of force sensors 56 may be used in accordance with the principles of the present disclosure. Force sensors 56 are configured to support base frame 52. More specifically, force sensors 56 are configured such that they provide complete and exclusive mechanical support for base frame 52 and all of the components that are supported on base frame 52 (e.g., lifts 26, litter frame 28, support deck 30, footboard 34, the headboard, siderails 36, etc.). Because of this construction, force sensors 56 are adapted to detect the weight of not only those components of person support apparatus 20 that are supported by the base frame 52 (including base frame 52 itself), but also any objects or persons who are wholly or partially being supported by support deck 30. By knowing the weight of the components of the person support apparatus 20, or by taring the scale before the patient enters the person support apparatus 20, a measurement of the weight of the patient may be obtained from the load cells. The outputs of force sensors 56 are part of an exit detection system 58 described in greater detail below.

In some alternative embodiments, person support apparatus 20 is constructed with load cells 56 positioned in locations other than base frame 52. For example, in at least one alternative embodiment, person support apparatus 20 is constructed with a litter frame and lift construction of the type disclosed in commonly assigned U.S. patent application Ser. No. 15/266,575 filed Sep. 15, 2016 by inventors Anuj K. Sidhu et al. and entitled PERSON SUPPORT APPARATUSES WITH EXIT DETECTION SYSTEMS, the complete disclosure of which is incorporated herein by reference. When person support apparatus 20 is constructed with the lift and litter frame construction of the type disclosed in this '575 application, the load cells 56 may be positioned on the top of the lifts such that the entire weight of the litter frame is supported on the load cells, as illustrated more clearly, for example, in FIGS. 2 and 3 of the aforementioned '575 application. Still other manners of positioning the load cells 56 within the person support apparatus 20, and/or other locations for the load cells 56, may be utilized.

Person support apparatus 20 comprises features for extending the width of its support deck 30 to accommodate patients of varying sizes. The width may be adjusted in any increments, for example between a first or minimum width, a second or intermediate width, and a third or expanded/maximum width. In one embodiment, person support apparatus 20 is configured to allow the support deck 30 to be adjusted to a first width of thirty-six inches, a second width of forty-two inches, and a third width of forty-eight inches, although these numerical values may, of course, take on different values in different embodiments. Further, support deck 30 may be configured to be adjustable to more than three different widths, in some embodiments, or less than three different widths in other embodiments.

In addition to being adjustable in width, person support apparatus 20 is adjustable in height via the lifts 26 adapted to raise and lower litter frame 28 with respect to base 22, as disclosed above. In further embodiments, the person support apparatus 20 may be adjustable in length, with the length between the head end 38 and foot end 40 being adjustable to accommodate patients of varying height.

As used herein, the term "longitudinal" refers to a direction parallel to an axis between the head end 38 and the foot end 40, where a head-to-foot distance is parallel to a longitudinal axis and is referred to as the length of the person support apparatus 20. The terms "transverse" or "lateral" refer to a direction perpendicular to the longitudinal direction and parallel to a surface on which the person support apparatus 20 rests, where a side-to-side distance is parallel to the transverse or lateral axis and is referred to as the width of the person support apparatus 20.

Figure 3:
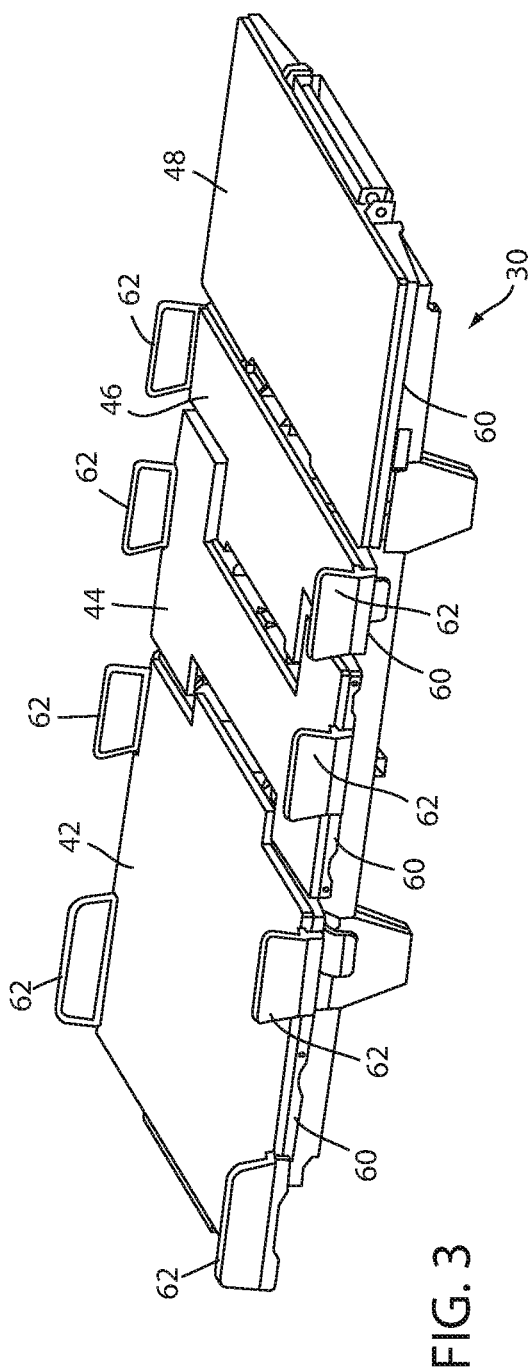
FIG. 3 is a perspective view of an adjustable width support deck of the person support apparatus of FIG. 1.
Figure 4:
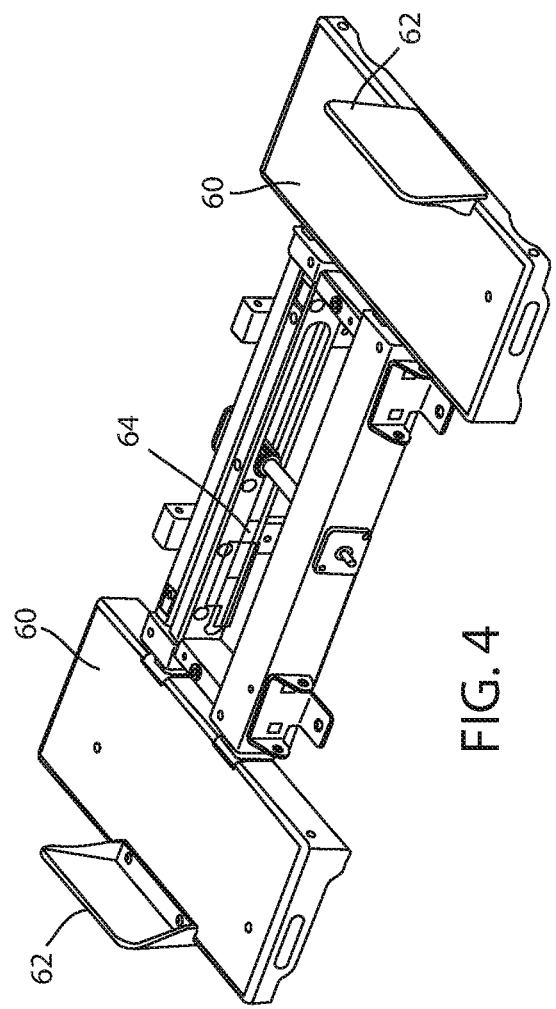
FIG. 4 is a perspective view of an expandable seat section of the adjustable width support deck of FIG. 3 showing elements for expanding and latching the seat section.

Referring to FIGS. 3-4, the width adjustable support deck 30 may comprise multiple expandable sections 60, or extension pans, which can be adjusted laterally by one or more length extendable actuators 64. The length extendable actuators 64 may be operated (extended or retracted) independently or together, and may be operated manually or automatically. Manually adjusting the width may be accomplished by pulling or pushing the support deck 30, optionally using handles 62 coupled to the sections 60, in a direction lateral to a longitudinal axis of the person support apparatus 20, the longitudinal axis extending between the head end 38 and the foot end 40. The support deck 30 may comprise any mechanism configured to permit manually adjusting the width of the support deck 30, for example a rack and pinion mechanism.

The head section 42, seat section 44, and thigh section 46 (and in some embodiments, foot section 48) comprise one or more pairs of expandable sections 60 which are positioned under the exposed top surface of deck section 42-46 (and 48, in some embodiments) when the support deck 30 is at its narrowest width. In one example shown in FIG. 4, taking the seat section 44 as an example, two deck sections 60 are linked by an extendible actuator 64, with the extension of the actuator 64 driving the linked deck sections 60 laterally in opposite directions to provide a wider surface. When the support deck 30 is expanded, the extension sections 60 that otherwise reside under the deck sections are exposed to provide an extended surface on which a larger mattress may rest. The litter frame 28 does expand with the support deck 30, and in some embodiments, the foot section 48 is not expandable.

In some embodiments, adjustable width deck 30 is constructed in any of the manners disclosed in commonly assigned U.S. patent application Ser. No. 62/887,977 filed Aug. 16, 2019, by inventors Jason Connell et al. and entitled PATIENT SUPPORT WITH DECK WIDTH MONITORING AND CONTROL, the complete disclosure of which is incorporated herein by reference. Other types of constructions of adjustable width deck 30 can, of course, be used.

It will also be understood by those skilled in the art that the non-deck portions of person support apparatus 20 can also or alternatively be designed with other types of mechanical constructions, such as, but not limited to, that described in commonly assigned, U.S. Pat. No. 10,130,536 to Roussy et al., entitled PATIENT SUPPORT USABLE WITH BARIATRIC PATIENTS, the complete disclosure of which is incorporated herein by reference. The mechanical construction of the non-deck portions of person support apparatus 20 may also take on forms different from what is disclosed in the aforementioned reference.

Figure 5:
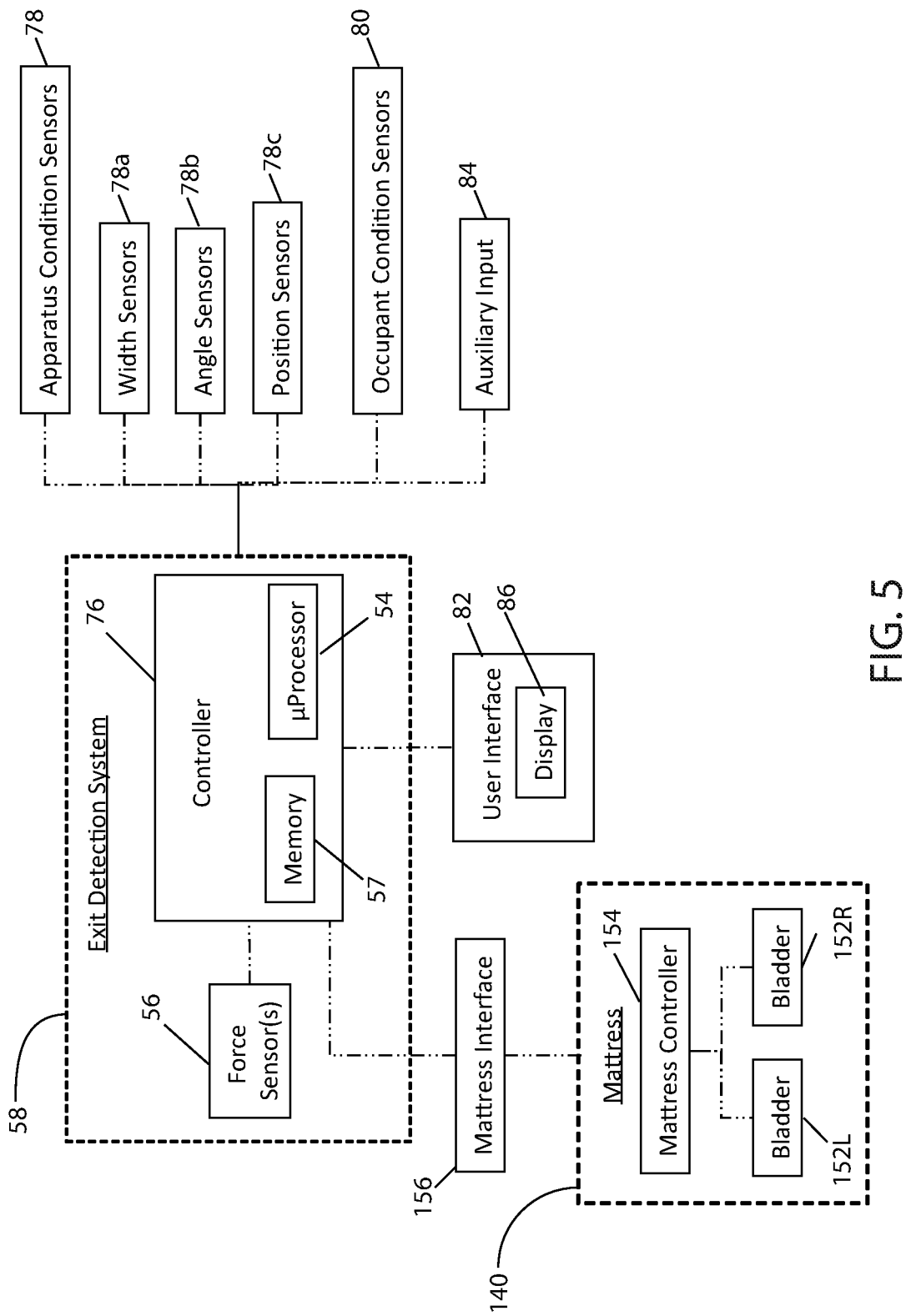
FIG. 5 is a block diagram of a portion of a control system of the person support apparatus of FIG. 1, including an exit detection system.

As shown in FIG. 5, person support apparatus 20 includes an exit detection system 58 that is adapted to determine when an occupant, such as, but not limited to, a patient, of person support apparatus 20 is moving and is likely to exit person support apparatus 20. More specifically, exit detection system 58 is adapted to determine when an occupant is leaving, or is likely to leave, and to issue an alert and/or notification to appropriate personnel so that proper steps can be taken in response to the occupant's departure, or imminent departure, in a timely fashion. The particular structural details of exit detection system 58 can vary widely. It will be understood by those skilled in the art that components of exit detection system 58 may be added or omitted from one or more of the embodiments of exit detection system 58 that are discussed herein.

In the embodiment shown in FIG. 5, exit detection system 58 includes force sensors 56 and a controller 76. Exit detection system 58 is in communication with one or more apparatus condition sensors 78 that detect a condition of person support apparatus 20, one or more occupant condition sensors 80 that detect a condition of an occupant of the person support apparatus 20, and a user interface 82. The condition sensors 78, 80 generate one or more output signals received by the controller 76. Based on the output signals received, the controller 76 can make an adjustment to an alert zone and/or an arming zone of the exit detection system 58, as will be discussed in greater detail below. Force sensors 56 may also be used to detect one or more conditions of the occupant, as the force sensors 56 may be used to detect a weight or center of gravity of an occupant of the person support apparatus 20, as described in further detail below. When forces sensors 56 are used to detect one or more of the occupant's conditions, a separate occupant condition sensor 80 may be omitted from exit detection system 58.

The condition sensors 78, 80 may take on any of a variety of different forms, including one or more load cells, pressure sensors such as piezoelectric and piezoresistive sensors, Hall Effect sensors, capacitive sensors, resonant sensors, thermal sensors, limit switches, gyroscopes, accelerometers, motion sensors, ultrasonic sensors, range sensors, potentiometers, magnetostrictive sensors, electrical current sensors, voltage detectors, and/or any other suitable types of sensors for carrying out their associated functions. Regardless of the specific form, the condition sensors 78, 80 report outputs to controller 76 and controller 76 uses the output, in at least some embodiments, to adjust an alert zone and/or an arming zone of the exit detection system 58.

Some non-limiting examples of condition sensors 78 include one or more width sensors 78a adapted to detect a deck width of the support deck 30, one or more angle sensors 78b adapted to detect an incline of the litter frame 28, or one or more position sensors 78c adapted to detect the position of one of the plurality of lifts 26. One or more additional apparatus condition sensors may be provided, such as a plurality of siderail sensors adapted to detect the position of each of the siderails 36. One manner of using siderail sensors to make an adjustment to an alert zone of an exit detection system is disclosed in commonly assigned U.S. Patent Application Publication No. 2017/0098359 to Sidhu et al., entitled PERSON SUPPORT APPARATUS WITH EXIT DETECTION SYSTEMS, the complete disclosure of which is incorporated herein by reference.

Width sensors 78a output signals that indicate a current width of the support deck 30. This width refers to a transverse or lateral dimension of the support deck 30 in a direction perpendicular to the longitudinal direction of person support apparatus 20. In some embodiments, width sensors 78a are coupled to each individual expandable section 60 such that the width of each section 60 is determined. In other embodiments, a single width sensors 78a may be utilized that collectively senses whether all of sections 60 are at a particular width or not. Still other variations of width sensors 78a may also or additionally be used.

Angle sensors 78b output signals that indicate a current incline angle of the litter frame 28, and can include tilt sensors or potentiometers for sensing an angular orientation of the litter frame 28, or any other suitable sensor for detecting the angular orientation of the litter frame 28.

Position sensors 78c are adapted to detect the position of one or more movable components of person support apparatus 20. In some embodiments, position sensors 78c are adapted to detect how far each lift 26 has extended. From this, controller 76 can determine an incline angle of the litter frame 28. In other embodiments, position sensors 78c can determine an angle of head section 42 (the Fowler section) relative to horizontal (or relative to one or more references on person support apparatus 20 itself). In still other embodiments, multiple types of position sensors 78c are included so that, for example, position sensors 78c report the current incline angle of the litter frame 28, height of litter frame 28, and head section angle to controller 76. In some embodiments, as will be discussed more below, controller 76 uses the position information from the one or more position sensors 78c as a factor in adjusting one or more zones of the exit detection system 58 and/or determining if the occupant is about to exit from person support apparatus 20.

Some non-limiting examples of condition sensors 80 include a vital sign sensor adapted to detect one or more vital signs of the occupant of person support apparatus 20. Force sensors 56 may also be used to detect one or more vital signs of the occupant. Manners for detecting the occupant's vital signs using force sensors 56 are disclosed in commonly assigned U.S. Pat. No. 7,699,784 to Wan Fong et al., entitled SYSTEM AND METHOD FOR MONITORING VITAL SIGNS, the complete disclosure of which is hereby incorporated herein by reference. One manner of using vital sign sensors to make an adjustment to an alert zone of an exit detection system is disclosed in commonly assigned U.S. Patent Application Publication No. 2017/0098359 to Sidhu et al., incorporated above.

Force sensors 56 are adapted to detect downward forces exerted by an occupant of support deck 30. Thus, when an occupant is positioned on support deck 30 and substantially still (i.e. not moving in a manner involving accelerations that cause forces to be exerted against support deck 30), force sensors 56 will detect the weight of the occupant (as well as the weight of any components of person support apparatus 20 that are supported—directly or indirectly—by force sensors 56). Force sensors 56 are also used to determine a center of gravity of the occupant, as will be discussed in greater detail below, in order to determine if the occupant is about to exit person support apparatus 20. In alternative embodiments, the outputs from force sensors 56 are analyzed, not to determine a center of gravity, but instead to determine a weight distribution and/or a change in weight distribution, such as by determining one or more ratios of the relative weights sensed by the force sensors 56 and using them to determine if the occupant is about to exit person support apparatus 20. In still other embodiments, force sensors 56 may be modified to detect forces other than, or in addition to, the downward forces exerted by the occupant. In yet other embodiments, the outputs from force sensors 56 are analyzed to determine if a non-occupant object has been added to or removed from the person support apparatus 20. Other types of sensors may also or alternatively be used for determining the occupant's weight.

Exit detection system 58 may also include one or more auxiliary inputs 84. Auxiliary inputs 84 are constructed as ports into which one or more sensors, cables, or other devices are coupled. The outputs from the sensors, cables, or other devices, are communicated to controller 76 and used as a factor, in some embodiments, in adjusting an alert zone and/or an arming zone of the exit detection system 58. The number of auxiliary inputs 84 may vary. Indeed, in some embodiments, exit detection system 58 includes no auxiliary inputs 84. However, when one or more auxiliary inputs 84 are included, such auxiliary inputs 84 may be configured in any of the following manners: as a wired port for coupling to a cable (e.g. an Ethernet port for coupling to an Ethernet cable, a USB port for coupling to a USB cable, a Controller Area Network (CAN) transceiver for coupling exit detection system 58 to a CAN bus, another type of embedded network port, etc.), as a port for coupling to a wireless transceiver (e.g. a Wi-Fi transceiver, a Bluetooth transceiver, a ZigBee transceiver, a near field communication (NFC) transceiver, etc.), as a port for coupling to one or more additional sensors, and/or as a port for coupling to other devices.

When coupled to an Ethernet cable or a Wi-Fi transceiver, one or more auxiliary inputs 84 may be used to communicate with, and receive information from, a healthcare facility local area network (LAN). More specifically, inputs 84 may receive information from an Electronic Medical Record (EMR) system that is in communication with the LAN. Such information may include any one or more of the following types of information about the occupant of person support apparatus 20: his or her gender, his or her height and/or weight, his or her fall risk assessment, and/or other information about the occupant. Exit detection system 58 optionally uses one or more of these items of information, in some embodiments, as factors in adjusting an alert zone and/or an arming zone of the exit detection system 58. One manner of using gender, height, weight, a fall risk assessment, and other information about the occupant to make an adjustment to an alert zone of an exit detection system is disclosed in commonly assigned U.S. Patent Application Publication No. 2017/0098359 to Sidhu et al., incorporated above. In some alternative embodiments, exit detection system 58 does not couple directly to the healthcare facility LAN, but instead communicates with one or more other components onboard person support apparatus 20 that are in communication with the LAN.

Controller 76 is constructed of any electrical component, or group of electrical components, that are capable of carrying out the functions described herein. In many embodiments, controller 76 is a conventional microcontroller, although not all such embodiments need include a microcontroller. In general, controller 76 includes any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 76 in carrying out the functions described herein, as well as the data necessary for carrying out these functions, are stored in a memory (not labeled) accessible to controller 76.

User interface 82 communicates with controller 76 and enables a user of person support apparatus 20 to control one or more aspects of person support apparatus 20, including exit detection system 58. User interface 82 is implemented in the embodiment shown in FIG. 1 as a control panel having a plurality of controls. The controls—which may be buttons, dials, switches, or other devices—allows a user to control various aspects of exit detection system 58, such as, but not limited to, selecting a mode of operation of exit detection system 58 and/or arming and disarming exit detection system 58. User interface 82 may also include a display 86 for displaying information regarding exit detection system 58. Display 86 may be a touchscreen that displays one or more controls and/or one or more of the control screens discussed below. Display 86 may comprise an LED display, OLED display, or another type of display.

Although FIG. 1 illustrates user interface 82 mounted to footboard 34, it will be understood that user interface 82 can be positioned elsewhere, and/or that one or more additional user interfaces can be added to person support apparatus 20 in different locations, such as the siderails 36, for controlling various aspects of exit detection system 58. In addition, one or more user interfaces may be communicatively coupled to person support apparatus 20 but physically positioned remote from person support apparatus 20, such as, but not limited to, a computer tablet, a smart phone, a computer station, etc.

Controller 76 of exit detection system 58 is adapted to determine the center of gravity of the occupant using the outputs from force sensors 56. Controller 76 uses this center of gravity to determine whether or not the occupant is about to exit from person support apparatus 20. In one embodiment, exit detection system 58 determines this center of gravity using the system and method disclosed in commonly assigned U.S. Pat. No. 5,276,432 to Travis, entitled PATIENT EXIT DETECTION MECHANISM FOR HOSPITAL BED, the complete disclosure of which is incorporated herein by reference. In other embodiments, other algorithms may be used.

Figure 6:
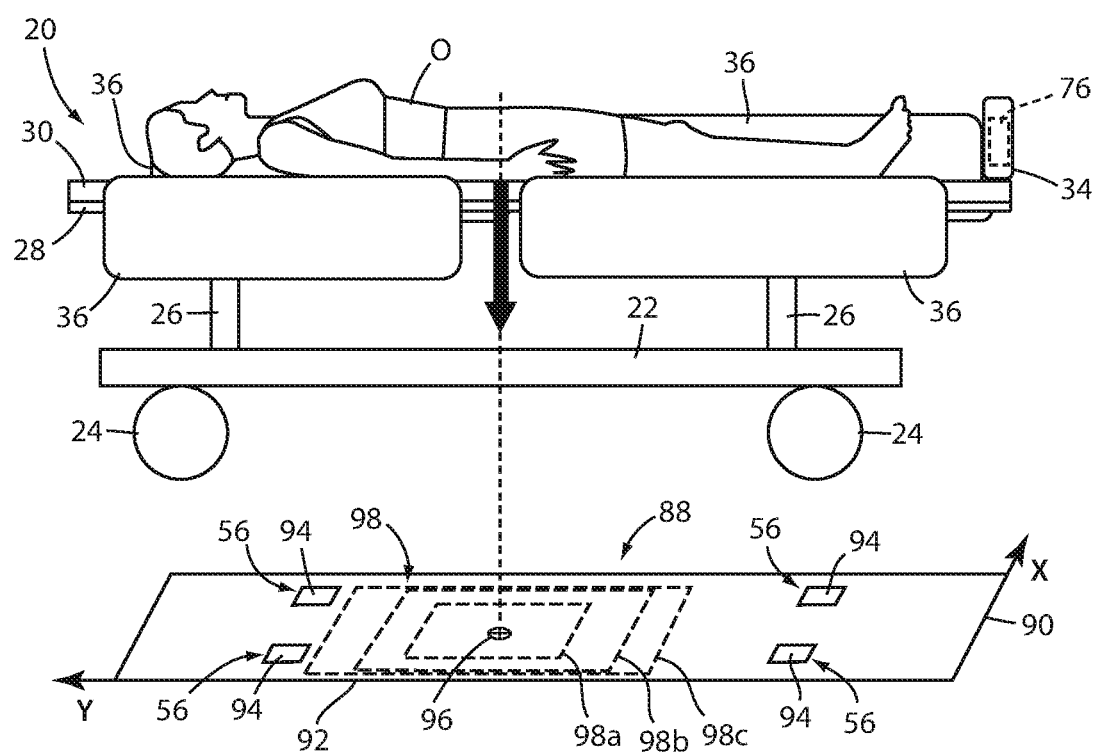
FIG. 6 is a diagram illustrating one manner in which the exit detection system of FIG. 5 determines if an occupant is about to exit or not.

As shown more clearly in FIG. 6 controller 76 determines the center of gravity of the occupant O in a planar coordinate frame of reference, such as reference frame 88. Reference frame 88 includes an X-axis 90 and a Y-axis 92. X-axis 90 is generally parallel to the footboard 34 of person support apparatus 20 while Y-axis 92 is generally parallel to a siderail 36, two of which are depicted in a lowered position in FIG. 6. Other coordinate systems can be used. Regardless of which coordinate system is used, controller 76 knows the location of force sensors 56 in the particular coordinate system that is used. In the example shown in FIG. 6, force sensors 56 are shown in known locations 94.

In the illustrative example shown in FIG. 6, controller 76 has determined the occupant's center of gravity to be at a location 96. Controller 76 compares this center of gravity 96 to the active alert zone 98 (explained in further detail below) that is defined in reference frame 88 and determines whether the center of gravity 96 is inside or outside of this alert zone 98. If center of gravity 96 moves outside of the alert zone 98, controller 76 issues an alert indicating that the occupant is about to exit from person support apparatus 20. When determining whether the center of gravity 96 is outside or inside of the alert zone 98, controller 76 may first compute the center of gravity in a first one of the directions of coordinate frame of reference 88 (X direction or Y direction), compare that value to the corresponding boundaries of the zone in that particular direction and, if it is inside the boundaries, compute the center of gravity in the other direction of coordinate frame of reference 88 (X direction or Y direction).

As shown in FIG. 6, there are three different alert zones 98a, b, and c. Alert zones 98a, b, and c have different sizes, allowing the occupant to engage in different amounts of movement prior to triggering an exit alert. A user selects which one of the alert zones 98a-c will be the active alert zone using user interface 82. Controller 76 then repetitively recalculates the occupant's center of gravity 96 based upon the outputs from force sensors 56 and compares the calculated center of gravity 96 to the active zone. If the center of gravity 96 is within the active alert zone 98, no exit alert is issued. If the center of gravity 96 moves outside of the active zone 98, controller 76 issues an alert. In some embodiments, in order to avoid issuing an alert based upon transient weight signals shifting the center of gravity 96 outside of the active zone 98 for a fleeting moment, controller 76 only issues an alert if the center of gravity 96 moves outside of the active zone 98 for more than a threshold amount of time (which may be on the order of seconds or a fraction of a second).

In some embodiments, controller 76 of exit detection system 58 is adapted to execute an arming process when it is initially armed and/or when it is already armed and a user switches the active zone from one zone to another. During the arming process, controller monitors movement of the occupant using the outputs from force sensors 56 and determines a center of gravity of the occupant. If the occupant moves too much, or moves outside of a specified region referred to herein as an arming zone, during the arming process, controller 76 does not arm the exit detection system 58 and notifies the user that the arming process failed. If, on the other hand, the occupant's movement levels remain below a threshold and the occupant's position remains within the arming zone, controller 76 completes the arming process and notifies the user that the exit detection system has been successfully armed. In the illustrated embodiment, there is a separate arming zone associated with each alerting zone.

Figure 7:
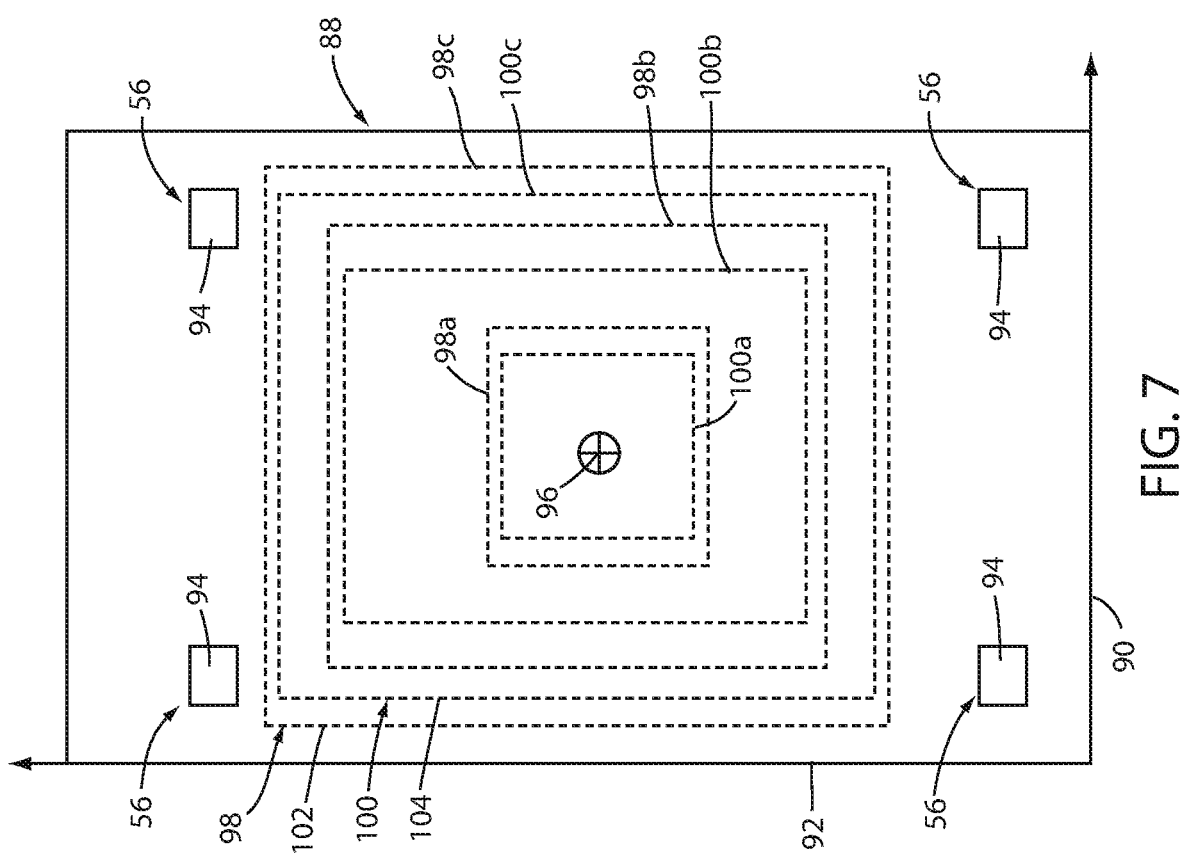
FIG. 7 is a plan view diagram of a reference frame for the person support apparatus of FIG. 1 showing multiple user-selectable zones for the exit detection system.

As shown more clearly in FIG. 7, controller 76 compares the center of gravity 96 of the occupant to the active one of arming zones 100 (i.e. the one corresponding to the alert zone selected by the user or caregiver) and determines whether the center of gravity 96 is inside or outside of this active zone 100 and if the occupant is settled or moving. If center of gravity 96 is outside of the active zone 100 (discussed below), controller 76 does not arm the exit detection system 58 and issues a notification indicating that the exit detection system 58 is unable to arm. When determining whether the center of gravity 96 is outside or inside of the active arming zone 100, controller 76 may first compute the center of gravity in a first one of the directions of coordinate frame of reference 88 (X direction or Y direction), compare that value to the corresponding boundaries of the zone in that particular direction and, if it is inside the boundaries, compute the center of gravity in the other direction of coordinate frame of reference 88 (X direction or Y direction). Alternatively, controller 76 may compute the center of gravity in both the X and Y directions and then compare the calculated center of gravity to the boundary defined by the arming zone 100.

If center of gravity 96 is inside of the active arming zone 100 (discussed below) but the occupant is not settled, controller 76 does not arm the exit detection system 58 and issues a notification indicating that the exit detection system 58 is unable to arm. When determining whether the occupant is settled or not settled, controller 76 may analyze output signals from the force sensors 56 to determine if the outputs change at a rate greater than a threshold speed for more than a threshold time (for example, on the order of 2 seconds). Once controller 76 determines the occupant is settled, controller 76 will arm the exit detection system 58. In some embodiments, in order to mitigate arming failures, if the occupant is not settled initially, controller 76 will continue to analyze the output signals for a longer period of time, or timeout period (for example, on the order of 15 seconds). If the occupant does not settle within the timeout period, controller 76 does not arm the exit detection system 58 and issues a notification indicating that the exit detection system 58 is unable to arm.

As shown in FIG. 7, there are three different arming zones 100a, b, and c. Arming zones 100a-c have different sizes, and are each associated with one of the three alert zones 98a-c of FIG. 6. In the example shown herein, alert zone 98a is associated with arming zone 100a, alert zone 98b is associated with arming zone 100b, and alert zone 98c is associated with arming zone 100c. Upon user-selection of one of the alert zones 98a-c to be the active alert zone using user interface 82, the associated arming zone 100a-c is automatically selected by controller 76 as the active arming zone.

Each zone 98, 100 has a boundary 102, 104 defining the area covered by the zone 98, 100, respectively. In the embodiment shown herein, the boundaries 102, 104 are indicated by dashed lines. When the exit detection system 58 is armed and an occupant of person support apparatus 20 moves such that his or her center of gravity 96 travels outside of the active alert zone 98, i.e. crosses the boundary 102, controller 76 issues an alert. To arm the exit detection system 58, the center of gravity 96 must be within the boundary 104 of the active arming zone 100 and the occupant settled. In still other embodiments, exit detection system 58 includes more zones 98, 100 than the three shown in FIG. 7, while in other embodiments, exit detection system 58 includes fewer zones than the three shown in FIG. 7 (including, in some embodiments, only a single alert zone 98 and arming zone 100).

Each arming zone 100a-c is smaller in size than its associated alert zone 98a-c, and has its boundary contained within a boundary of the associated alert zone 98a-c. Although FIGS. 6-7 illustrate each alert zone 98a-c and arming zone 100a-c as having a generally rectangular shape, it will be understood that the alert zones 98a-c and arming zones 100a-c do not all have to have the same shape. Further, it will also be understood that any one or more of the zones can be shaped in other manners besides rectangles. In some embodiments, any one or more of the zones 98, 100 are squares, parallelograms, other quadrilaterals, circles, ovals, or any combination of arcs, straight lines, curves, and/or other shapes.

Figure 8:
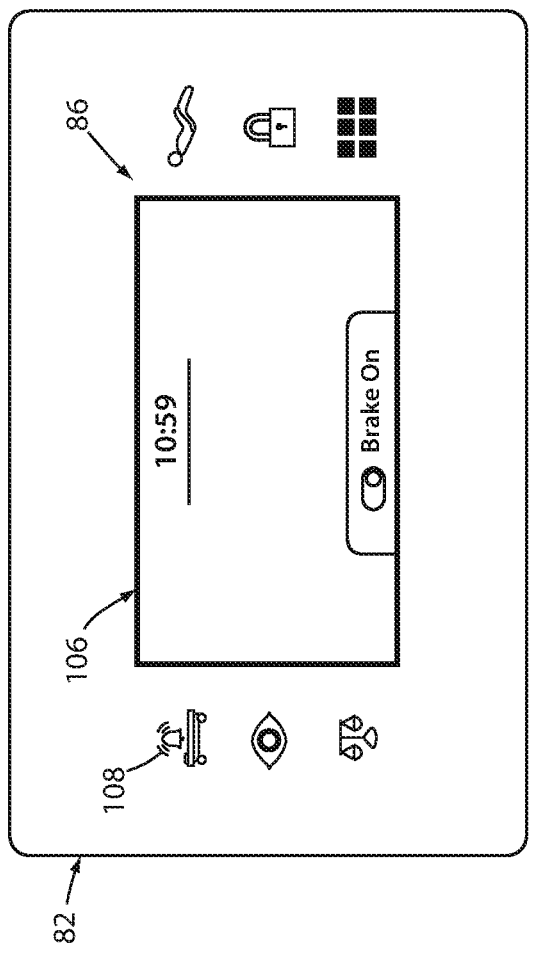
FIG. 8 is a plan view of a portion of a user interface for the person support apparatus of FIG. 1, the user interface displaying an arbitrary screen and including a control for arming the exit detection system.
Figure 9:
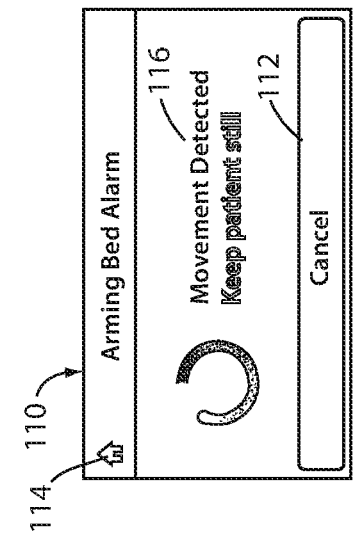
FIG. 9 is a schematic view of an arming screen configured to be displayed on the user interface of FIG. 8 during arming of the exit detection system.

As noted, user interface 82 includes an arming control that enables a user to turn exit detection system 58 on and off (arm and disarm exit detection system 58), as well as allowing a user to select different modes which are used for arming the system and triggering an exit alert. FIG. 8 depicts a portion of the user interface 82 (FIG. 1) including the display 86. Display 86 is configured to display a plurality of different screens thereon, one of which (screen 106) is shown in FIG. 9. The user interface 82 includes controls for accessing all of the functionality of person support apparatus 20, including the exit detection system 58. For example, user interface 82 includes an arming control 108 for arming exit detection system 58. Upon user-activation of the arming control 108, controller 76 is operable to arm exit detection system 58. The arming control 108 can optionally show the status of the exit detection system 58, such as by illuminating in green when the exit detection system 58 is armed.

While the exit detection system 58 attempts to arm, an arming screen 110, such as that shown in FIG. 9, is displayed on the display 86 of the user interface 82. From this screen 110, the caregiver can cancel the arming attempt by selecting a cancel control 112, or can return to a home screen by selecting a home control 114. While waiting for the occupant to settle, the arming screen 110 can optionally show a message 116 indicating that the occupant must settle before the system will arm (i.e., "Movement Detected; Keep patient still").

Figure 10:
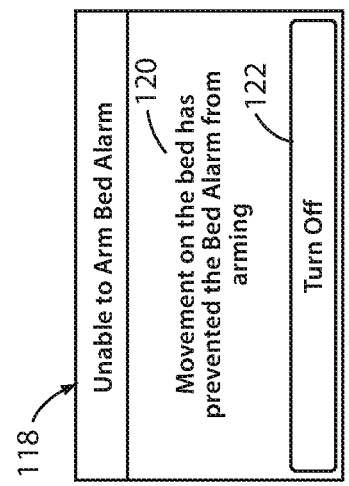
FIG. 10 is a schematic view of a failure screen configured to be displayed on the user interface of FIG. 8 if the exit detection system fails to arm.

If the exit detection system 58 fails to arm, a failure screen 118 shown in FIG. 10 is displayed on the display 86 of the user interface 82. The failure screen 118 includes a message 120 notifying the caregiver that the exit detection system 58 has failed to arm, as well as a reason for the failure to arm (i.e., "Movement on the bed has prevented to Bed Alarm from arming"). From this screen 118, the caregiver can turn off the failure notification and return to the home screen by selecting a turn off control 122.

Figure 11:
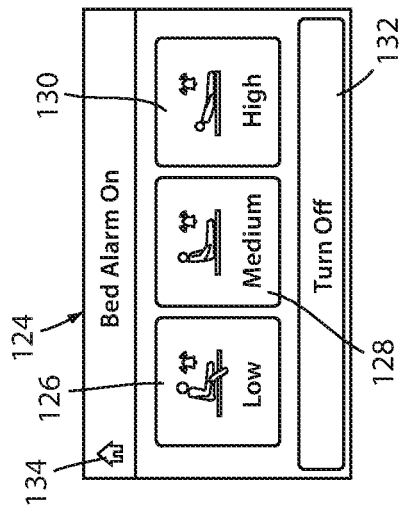
FIG. 11 is a schematic view of a control screen for the exit detection system configured to be displayed on the user interface of FIG. 8.

If the exit detection system 58 successfully arms, or if the user cancels the arming attempt by selecting cancel control 112 (FIG. 9), a control screen 124 shown in FIG. 11 is displayed on the display 86 of the user interface 82. From this control screen 124, the caregiver can select an alert mode using mode controls 126, 128, 130, can select to turn off or disarm the exit detection system 58 by selecting a turn off control 132, or can return to the home screen by selecting a home control 134. It is noted that if the exit detection system 58 is already armed, selecting the arming control 108 on the user interface 82 will also display control screen 124.

The mode of exit detection system 58 can be set to low, medium, or high using mode controls 126, 128, 130. The modes correspond to the alert zones 98a-c of person support apparatus 20 that are monitored by exit detection system 58. By selecting one of the modes, the user selects which one of the alert zones 98a-c will be the active alert zone, and the associated arming zone 100a-c is automatically selected as the active arming zone. For example, with the "high" mode control 130 selected, exit detection system 58 monitors the first, smallest zone 98a at or near the center of the support deck 30. With the "medium" mode control 128 selected, exit detection system 58 monitors the second zone 98b at or near the center of the support deck 30 which is larger than the first zone 98a. With the "low" mode control 126 selected, exit detection system 58 monitors the third zone 98c at or near the center of the support deck 30, which is larger than both the first and second zones 98a, 98b. When first armed for a new patient, the default state for the exit detection system 58 is the medium mode.

Returning to FIG. 7, the boundary 102,104 of at least one of the zones 98, 100 is dynamic. That is, at least one of the zones 98, 100 has a size, shape, and/or location that varies based upon one or more criteria that will be discussed more below. In some embodiments, all of the boundaries 102, 104 are dynamic.

Controller 76 can adjust the boundary 102,104 of at least one of the dynamic zones 98, 100 by changing a shape of the boundary 102,104, changing a dimension of the boundary 102,104, changing an area defined within the boundary 102,104, changing a location of the boundary 102,104, or any combination thereof. Changing a shape of the boundary 102,104 may include moving at least one portion of the boundary 102,104 laterally, longitudinally, or a combination thereof, and/or changing between various polygonal shapes, including rectangular, square, parallelogram, other quadrilaterals, circle, oval, or any combination of arcs, straight lines, curves, and/or other shapes. Changing a dimension of the boundary 102,104 may include increasing or decreasing a width or length of the zone 98, 100. Changing an area defined within the boundary 102,104 may include increasing or decreasing the size of the zone 98, 100. Changing a location of the boundary 102,104 may include shifting the boundary 102, 104 while optionally maintaining the same shape or area for the zone 98. 100.

Some of the criteria used by controller 76 to vary the boundary 102, 104 of one or more zones 98, 100 include the following: (a) the width of the support deck 30 of person support apparatus 20; (b) an incline angle of the litter frame 28; (c) the status of a lateral rotation therapy; and (d) the addition or removal of a non-occupant object. Some additional the factors or criteria used by controller 76 to vary the boundary 102, 104 of one or more zones 98, 100 include the following: (a) the weight of the occupant; (b) the height of the occupant; (c) a ratio of the occupant's height and weight; (d) the gender of the occupant; (e) a fall risk assessment of the occupant; (f) values of one or more vital signs of the occupant; (g) a position of the siderails 36; (h) a downward force being applied to one or more of the siderails 36; (i) a position or orientation of one or more other components of person support apparatus 20; (j) the environment or surroundings in which person support apparatus 20 is positioned; (k) a proximity of a caregiver to person support apparatus 20; (l) a time of day; (m) one or more medical conditions of the occupant; (n) a body orientation of the occupant; (o) a current height of litter frame 28, (p) movement of the occupant (e.g. sitting up), and/or other factors. It will be understood that controller 76 is programmed in some embodiments to use only a single one of these factors, while in other embodiments controller 76 is programmed to use any two or more of these of the factors in any possible combination.

In some embodiments of exit detection system 58, the user of person support apparatus 20, such as the caregiver, can use user interface 82 to select the individual factors that are to be used by exit detection system 58, or to select one or more predetermined combinations of factors that are to be used by exit detection system 58 when determining whether to issue an exit alert or not. In other embodiments, the particular combination of factors used by exit detection system 58 is preprogrammed. In still other embodiments, exit detection system 58 includes one or more user-selectable modes in which one or more preprogrammed combinations of factors are used by controller 76 to determine if an exit alert should be issued, but also includes one or more user-selectable modes that allow the user to customize the factors used by controller 76 when determining if an exit alert should be issued or not.

In at least one embodiment in which controller 76 is configured to adjust the boundary 102 of an alert zone 98 based on the height of litter frame 28, controller 76 receives signals from lifts 26 (and/or from the motor controller that oversees operation of lifts 26) and uses those signals to determine a current height of litter frame 28. In this embodiment, controller 76 contracts the size of the currently active alert zone 98 when the higher litter frame 28 is raised. Similarly, when litter frame 28 is lowered, controller 76 expands the size of the currently active alert zone 98. Controller 76 applies this height-based expansion and contraction only to the medium and large alert zones 98b and 98c, and keeps small alert zone 98a at a constant size, regardless of litter height.

Figure 14:
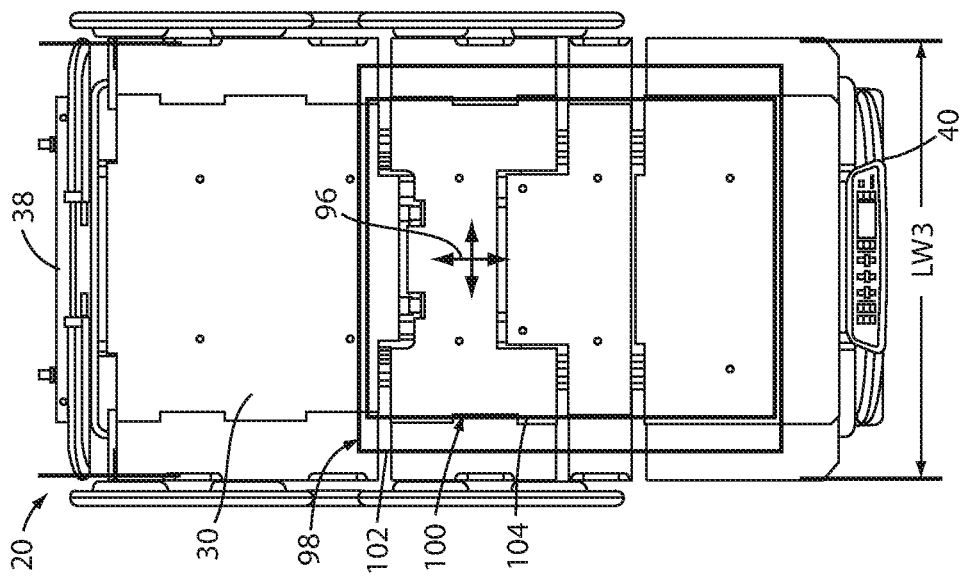
FIG. 14 is a plan view diagram of the person support apparatus of FIG. 12 showing another modification of the zones in response to the support deck expanding to a third width greater than the second width of FIG. 13.
Figure 13:
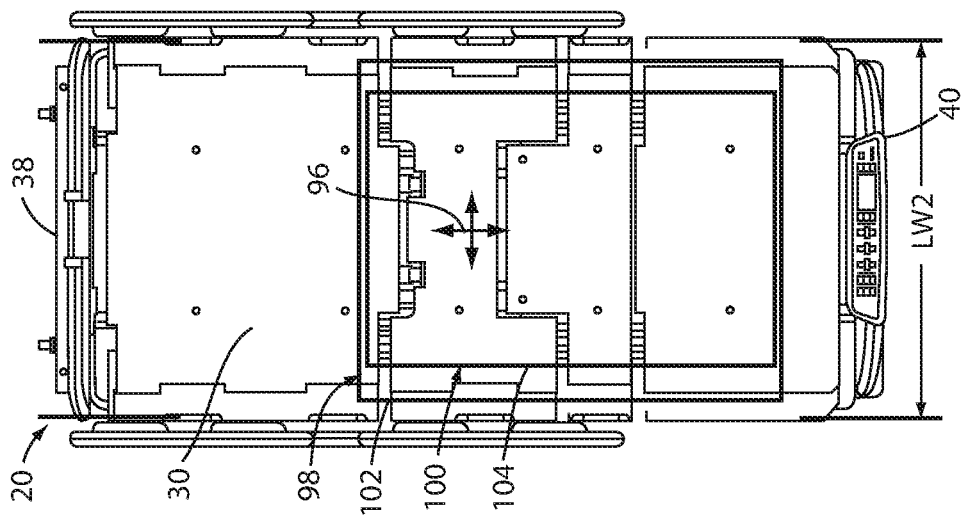
FIG. 13 is a plan view diagram of the person support apparatus of FIG. 12 showing a modification of the zones in response to the support deck expanding to a second width greater than the first width of FIG. 12.
Figure 12:
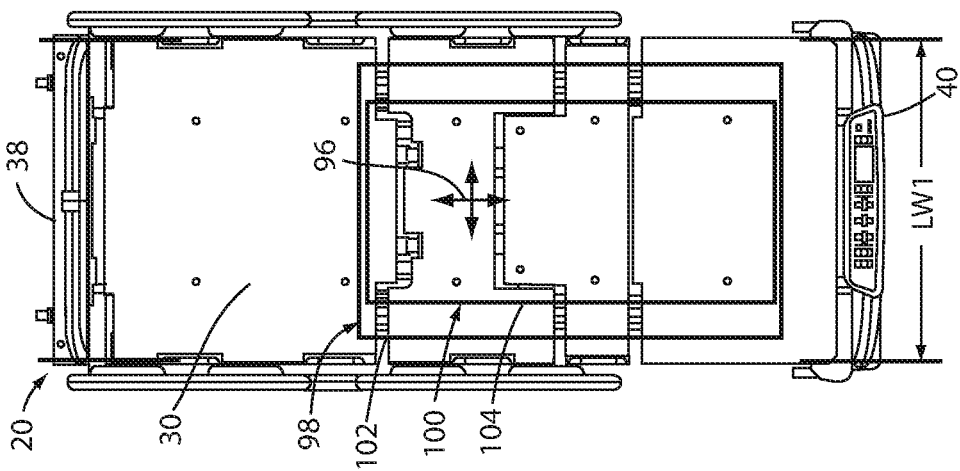
FIG. 12 is a plan view diagram of the person support apparatus illustrating an alert zone used to trigger an exit alarm and an arming zone used to arm the exit detection system, shown with the support deck in a first width.

FIGS. 12-14 illustrate one manner in which controller 76 adjusts the boundary 102, 104 of the zones 98, 100 in response to the width of the support deck 30 being changed. FIG. 12 illustrates the person support apparatus 20 with support deck 30 at a first or minimum width LW1, with alert zone 98 defined by boundary 102 and arming zone 100 defined by boundary 104. When an occupant of person support apparatus 20 moves such that his or her center of gravity 96 travels outside of alert zone 98, i.e. crosses the boundary 102, controller 76 issues an alert. When the center of gravity 96 of the occupant is inside of arming zone 100, i.e. within the boundary 104, controller 76 may arm the exit detection system 58.

As can be seen in FIG. 13, when the width of support deck 30 is increased to a second or intermediate width LW2, controller 76 increases the size of the alert zone 98 by moving the boundary 102 outward along at least one side of the alert zone 98 to increase the area covered by the alert zone 98. This allows the occupant's center of gravity 96 to approach the sides of the person support apparatus 20 more closely than it otherwise could (if the alert zone 98 remained the same as shown in FIG. 12) without triggering an exit alert. Controller 76 also increases the size of the arming zone 100 by moving the boundary 104 outward along at least one side of the arming zone 100 to increase the area covered by the arming zone 100. This allows the occupant's center of gravity 96 to be within a wider area of the person support apparatus 20 than it otherwise could (if the arming zone 100 remained the same as shown in FIG. 12) while still permitting arming of the exit detection system 58.

As can be seen in FIG. 14, when the width of the support deck 30 is increased to a third or maximum width LW3, controller 76 increases the size of the alert zone 98 by moving the boundary 102 outward along at least one side of the alert zone 98 to increase the area covered by the alert zone 98. This allows the occupant's center of gravity 96 to approach the sides of the person support apparatus 20 more closely than it otherwise could (if the alert zone 98 remained the same as shown in FIG. 12 or in FIG. 13) without triggering an exit alert. Controller 76 also increases the size of the arming zone 100 by moving the boundary 104 outward along at least one side of the arming zone 100 to increase the area covered by the arming zone 100. This allows the occupant's center of gravity 96 to be within a wider area of the person support apparatus 20 than it otherwise could (if the arming zone 100 remained the same as shown in FIG. 12 or in FIG. 13) while still permitting arming of the exit detection system 58.

With respect to the width of support deck 30, exit detection system 58 receives this information either directly from width sensors 78a or it is input into exit detection system 58. When input, it may be input via a caregiver entering the width information via user interface 82, or it may be input by communicating with length extendable actuators 64, 68. Regardless of the source of the width data, controller 76 uses this information to adjust one or more of the zones 98, 100. That is, controller 76 uses the width to adjust one or more of the boundaries 102, 104 of one or more of the zones 98, 100 based upon this width.

In some embodiments, the adjustments to the width of the zone 98, 100 made in response to changes in the deck width are made incrementally based upon one or more predefined ranges of width. For example, a support deck width falling anywhere within a first range can cause controller 76 to adjust the width of the zones 98, 100 by a first amount, support deck widths falling anywhere within a second range can cause controller 76 to adjust the width of the zones 98, 100 by a second amount, etc. In some embodiments, only two ranges are used, while in other embodiments, other numbers of ranges are used.

Controller 76 is also programmed in some embodiments to change the height of one or more zones 98, 100 based upon the width of person support apparatus 20. In other embodiments, controller 76 only changes the width of one or more zones 98, 100, or changes both the height and width based upon the width of person support apparatus 20. The height of a zone refers to the length of the zone from a point on its boundary closest to head end 38 to a point on its boundary closest to foot end 40.

Although FIGS. 12-14 illustrate only a single alert zone 98 and a single arming zone 100, it will be understood that, in some embodiments, controller 76 changes the size, shape, and/or location of multiple zones in response to the changing width. Further, it will be understood that the adjustment in size of the zones 98, 100 illustrated in FIGS. 12-14 are merely one example of the types of zone adjustments that may be implemented by controller 76 in response to the changing width. Other types of zone adjustments are also possible, including an adjustment in shape and/or location.

In some embodiments, controller 76 is configured to only expand the width of an alert zone 98 in response to an expansion of the deck 30 if all of the sections of the deck 30 are expanded. In such embodiments, if the user only expands, say, the width of seat section 44 from its minimum width to its intermediate width and the width of the other sections of support deck 30 (e.g. sections 42, 46, and 48) remain at their minimum width, controller 76 keeps zone 100 at its narrowest width (e.g. the width shown in FIG. 12). Similarly, controller 76 is configured in some embodiments to automatically reduce the width of the alert zone 98 if any one of the sections of support deck 30 are contracted. Thus, for example, if all of the deck sections are at their maximum width (e.g. FIG. 14) and a user contracts head section 42 to its intermediate width, controller 76 automatically contracts the alert zone 98 to its intermediate size (e.g. what is shown in FIG. 13). Further, if the user contracts head section 42 to its narrowest width (while the other sections of support deck 30 remain at their widest width), controller 76 automatically contracts alert zone 98 to its narrowest size (e.g. what is shown in FIG. 12).

In an alternative embodiment, controller 76 is configured to adjust the alert zone 98 in response to each section of deck 30 being expanded or contracted. Thus, for example, if only seat section 44 is expanded, controller 76 is configured to make an adjustment to zone 98 that takes into account the lone expansion of seat section 44. In this embodiment, if, after seat section 44 is expanded, the user subsequently expands, say, head section 42 to the same width as the seat section 44, controller 76 is configured to make another adjustment to zone 98 that takes into account this expansion of head section 42. In this fashion, controller 76 is configured to make piecemeal adjustments to the alert zone 98 based upon each individual section of support deck 30 that is widened or narrowed.

Figure 17:
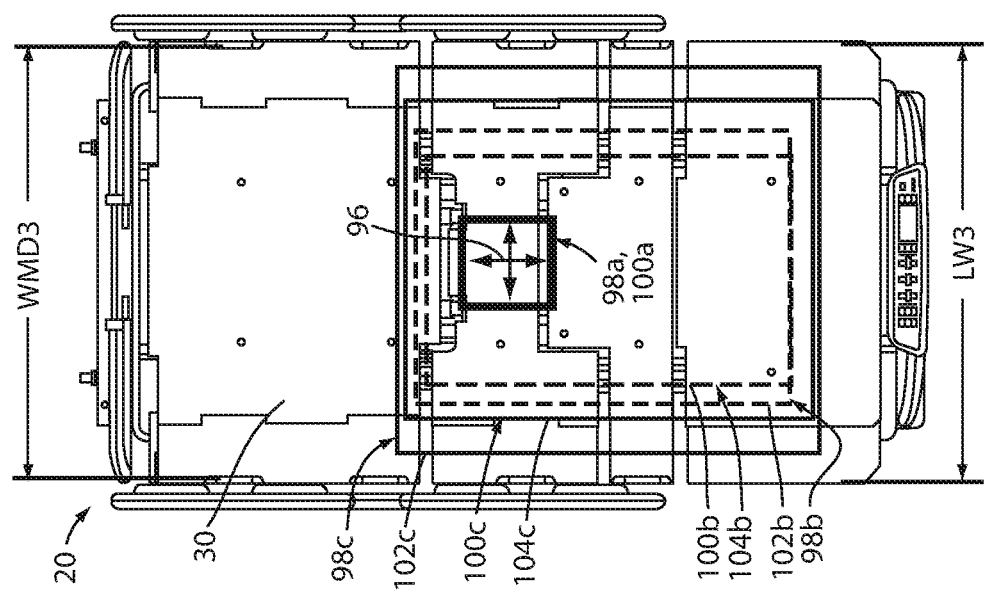
FIG. 17 is a plan view diagram of the person support apparatus of FIG. 15 showing another modification of multiple zones in response to the support deck expanding to a third width.
Figure 16:
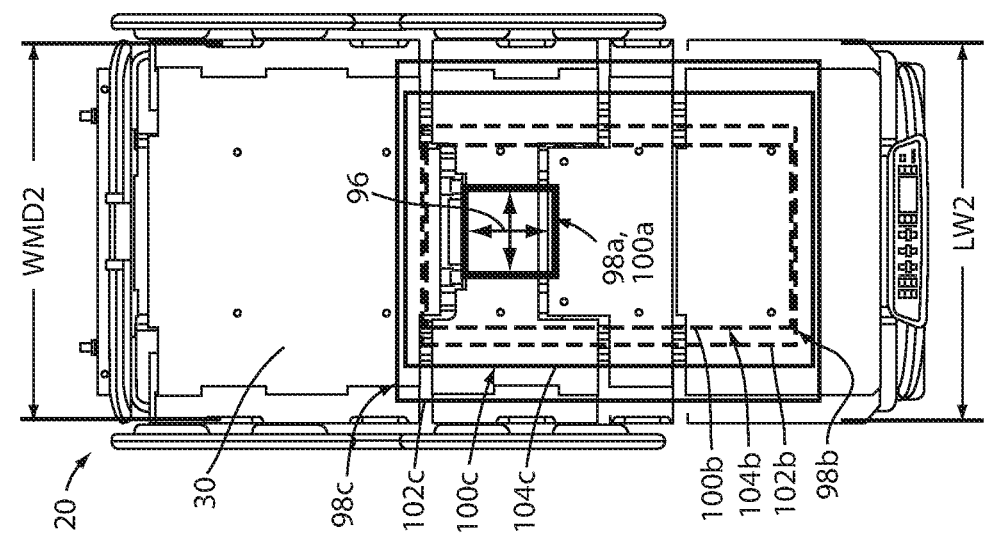
FIG. 16 is a plan view diagram of the person support apparatus of FIG. 15 showing a modification of multiple zones in response to the support deck expanding to a second width.
Figure 15:
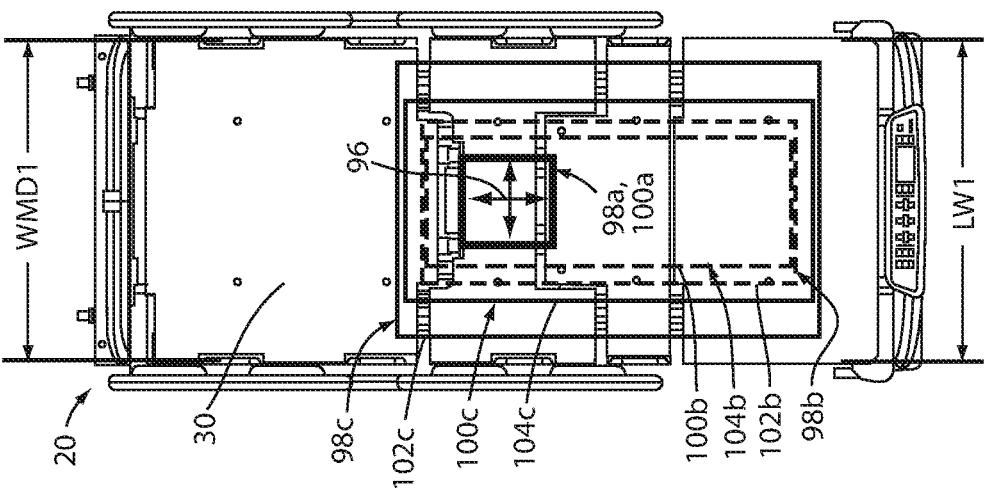
FIG. 15 is a plan view diagram of the person support apparatus illustrating multiple user-selectable alert zones and associated arming zones, shown with the support deck in a first width.

FIGS. 15-17 illustrate one manner in which controller 76 adjusts the boundary 102, 104 of multiple user-selectable zones in response to the deck width being changed. As can be seen, when the width of deck 30 is increased to the second or intermediate width LW2 or to the third or maximum width LW3, controller 76 increases the size of multiple alert zones 98*b*, 98*c* by moving their boundaries 102*b*, 102*c* outward along at least one side of the zones 98*b*, 98*c* to increase the area covered by the zones 98*b*, 98*c*. Controller 76 also increases the size of multiple arming zones 100*b*, 100*c* by moving their boundaries 104*b*, 104*c* outward along at least one side of the arming zones 100*b*, 100*c* to increase the area covered by the arming zones 100*b*, 100*c*.

In at least one embodiment, at least one of the multiple user-selectable zones is not adjusted in response to the deck width being changed. Specifically, controller 76 adjusts the boundaries 102*b*, 102*c*, 104*b*, 104*c* of those zone(s) 98*b*, 98*c*, 100*b*, 100*c* that have a dynamic boundary. Those zone(s) that have a static boundary, i.e. zones 98*a*, 100*a*, do not have their boundaries adjusted. As can be seen in FIGS. 15-17, zones 98*a* and 100*a* correspond to the smallest alert zone 98*a* and arming zone 100*a*, which correspond to the "high" alert mode selectable by the caregiver in FIG. 11.

In one embodiment, while zones 98*a*, 100*a* are static with respect to changes in the width of the support deck 30, the initial location of zones 98*a*, 100*a* is dynamic with respect to the patient's center of gravity at the time exit detection system 58 is initially armed, or at the time the user switches the active zone of an already armed exit detection system 58 from one of the other zones 98*b* or 98*c* to zone 98*a*. That is, zones 98*a* and 100*a* are centered at a location corresponding to the patient's center of gravity at the time exit detection system 58 is armed with zone 98*a* as the active zone, or at the time the user selects zone 98 as the active zone. Once defined at this location, zones 98*a* and 100*a* do not change their size, shape, or location in response to changes in the width of support deck 30. In fact, in some embodiments, controller 76 does not thereafter adjust zones 98*a* and 100*a* for any reason other than if exit detection system 58 is disarmed and later re-armed, or the user selects another zone 98*b* or 98*c* to be the active zone and thereafter re-selects zone 98*a* again as the active zone.

In the aforementioned embodiment, controller 76 is configured to not change the initial location of zones 98*b* or 98*c* (or 100*b* or 100*c*) based on the patient's center of gravity at the time exit detection system 58 is armed. That is, regardless of where the patient is currently located when one of zones 98*b* or 98*c* is initially armed, or changed to be the current active zone, controller 76 defines the location of these zones in a manner that is fixed with respect to geometry of person support apparatus 20. As a result, controller 76 is configured, in at least one embodiment, to initially define (at the moment of arming or activation) the location of zones 98*b* and 98*c* in a manner independent of the patient's position at that time, and to subsequently adjust zones 98*b* and 98*c* based on changes to the width of support deck 30. In that same embodiment, controller 76 is configured to initially define at the moment of arming or activation) the location of zone 98*a* in a manner that is dependent of the patient's position at that time, and to subsequently not adjust the size, shape, or location of zone 98*a* in response to changes to the width of support deck 30.

FIGS. 18-20 illustrate one manner in which controller 76 adjusts the boundary 102, 104 of the zones 98, 100 in response to the incline angle of litter frame 28 of the person support apparatus 20 being changed. As shown in the figures, the litter frame 28 can be tilted or inclined relative to the base 22 by controlling the height of lifts 26. In FIG. 18, the incline angle is zero since the litter frame 28 is oriented horizontally. Using reference frame 88, alert zone 98 is defined by boundary 102 and arming zone 100 is defined by boundary 104. When an occupant of person support apparatus 20 moves such that his or her center of gravity 96 travels outside of alert zone 98, i.e. crosses the boundary 102, controller 76 issues an alert. When the center of gravity 96 of the occupant remains inside of arming zone 100 during the arming process of exit detection system 58, controller 76 is adapted to allow the exit detection system 58 to be armed.

As can be seen in FIG. 19, when the litter frame 28 is inclined to elevate the foot end 40 above the head end 38, i.e. moved to a Trendelenburg orientation, controller 76 adjusts the boundary 102 of the alert zone 98 by moving at least one point of the boundary 102 closer to the head end 38. The boundary 102 can have its longitudinal length increased in the direction of head end 38 to increase the area covered by the alert zone 98, or the entire boundary 102 can be moved toward the head end 38 to relocate the alert zone 98 closer to the head end 38 without changing the overall size of the zone 98. Either option allows the occupant's center of gravity 96 to approach the head end 38 of the person support apparatus 20 more closely than it otherwise could (if the alert zone 98 remained the same as shown in FIG. 18) without triggering an exit alert.

Controller 76 also adjusts the boundary of the arming zone 100 by moving at least one portion of the boundary 104 closer to the head end 38. The boundary 104 can have its longitudinal length increased in the direction of head end 38 to increase the area covered by the arming zone 100, or the entire boundary 104 can be moved toward the head end 38 to relocate the arming zone 100 closer to the head end 38 without changing the overall size of the zone 100. Either option allows the occupant's center of gravity 96 to be closer to the head end 38 than it otherwise could (if the arming zone 100 remained the same as shown in FIG. 18) while still permitting arming of the exit detection system 58.

As can be seen in FIG. 20, when the litter frame 28 inclined to elevate the head end 38 above the foot end 40, i.e. moved to a reverse Trendelenburg orientation, controller 76 adjusts the boundary 102 of the alert zone 98 by moving at least one point of the boundary 102 closer to the foot end 40. The boundary 102 can have its longitudinal length increased in the direction of foot end 40 to increase the area covered by the alert zone 98, or the entire boundary 102 can be moved toward the foot end 40 to relocate the alert zone 98 closer to the foot end 40 without changing the overall size of the zone 98. Either option allows the occupant's center of gravity 96 to approach the foot end 40 of the person support apparatus 20 more closely than it otherwise could (if the alert zone 98 remained the same as shown in FIG. 18) without triggering an exit alert.

Controller 76 also adjusts the boundary of the arming zone 100 by moving at least one portion of the boundary 104 closer to the foot end 40. The boundary 104 can have its longitudinal length increased in the direction of foot end 40 to increase the area covered by the arming zone 100, or the entire boundary 104 can be moved toward the foot end 40 to relocate the arming zone 100 closer to the foot end 40 without changing the overall size of the zone 100. Either option allows the occupant's center of gravity 96 to be closer to the foot end 40 than it otherwise could (if the arming zone 100 remained the same as shown in FIG. 18) while still permitting arming of the exit detection system 58.

With respect to the incline of the person support apparatus 20, exit detection system 58 receives this information either directly from angle sensors 78b, position sensors 78c, or it is input into exit detection system 58. When input, it may be input via a caregiver directly entering the incline angle information via user interface 82, or it may be input by a caregiver selecting a position control, for example a one-touch input control to move the person support apparatus 20 to the Trendelenburg orientation or reverse Trendelenburg orientation. Regardless of the source of the angle data, controller 76 uses this information to adjust one or more of the zones 98, 100. That is, controller 76 uses the angle to adjust one or more of the boundaries 102, 104 of one or more of the zones 98, 100 based upon this angle.

In one embodiment, controller 76 adjusts the location of the boundary 102, 104 of a zone 98, 100 based upon the current incline angle of person support apparatus 20. Adjusting the location of the boundary 102, 104 as the person support apparatus 20 is tilted will allow the occupant's center of gravity 96 to move closer to the head end 38 or foot end 40 of person support apparatus 20 without triggering an exit alert, or it will prevent the occupant from moving as close to the ends 38, 40 of the person support apparatus 20 before triggering an exit alert.

In some embodiments, controller 76 moves a zone 98, 100 to a predetermined location in response to movement of the person support apparatus 20 to the Trendelenburg orientation or reverse Trendelenburg orientation. That is, the zone 98, 100 is moved to a first location when the person support apparatus 20 is in the Trendelenburg orientation and the zone 98, 100 is moved to a second location when the person support apparatus 20 is in the reverse Trendelenburg orientation.

Controller 76 is also programmed in some embodiments to change the shape of one or more zones 98, 100 based upon the incline angle of litter frame 28. For example, the boundary 102, 104 of the zone 98, 100 can be widened near the head end 38 when the person support apparatus 20 is in the Trendelenburg orientation and the boundary 102, 104 of the zone 98, 100 can be widened near the foot end 40 when the person support apparatus 20 is in the reverse Trendelenburg orientation.

Although FIGS. 18-20 illustrate only a single alert zone 98 and a single arming zone 100, it will be understood that, in some embodiments, controller 76 changes the size, shape, and/or location of multiple zones in response to the changing incline of the litter frame 28. Further, it will be understood that the adjustment in size of the zones 98, 100 illustrated in FIGS. 18-20 are merely one example of the types of zone adjustments that may be implemented by controller 76 in response to the changing incline angle. Other types of zone adjustments are also possible, including an adjustment in location and/or shape.

In at least one embodiment, the distance that controller 76 shifts the zone 98 toward the head end 38 or foot end 40 in response to changes in the incline of litter frame 28 is determined based the distance the patient's measured center of gravity changes due solely to the change in incline angle. In other words, controller 76 is configured to use a known trigonometric ratio to calculate the distance the center of gravity of the patient moves based solely upon changes in the incline of the litter frame 28, and to use this distance to adjust the length or position of zone 98 toward head end 38 or foot end 40.

Figure 22:
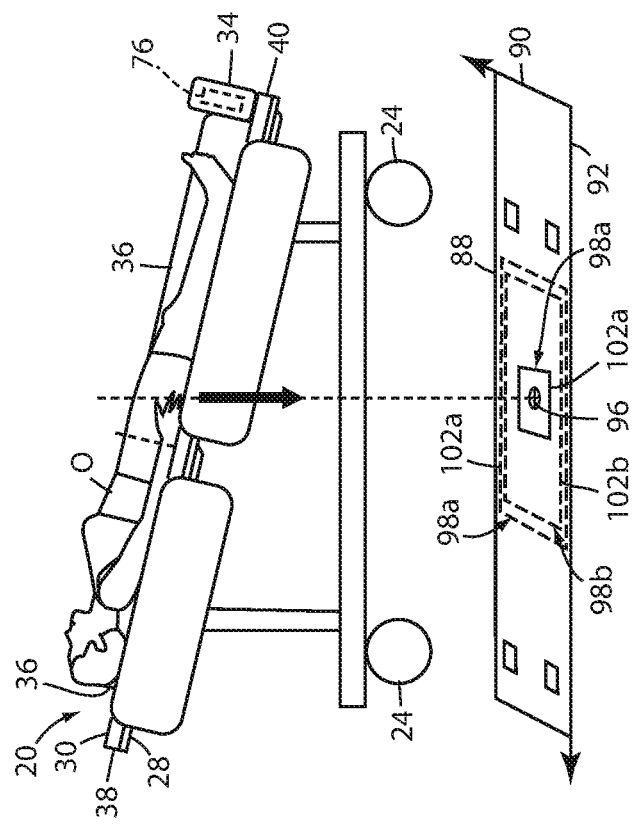
FIG. 22 is a diagram of the person support apparatus of FIG. 18 showing another modification of the multiple user-selectable zones in response to the litter frame moving to a reverse Trendelenburg orientation.
Figure 21:
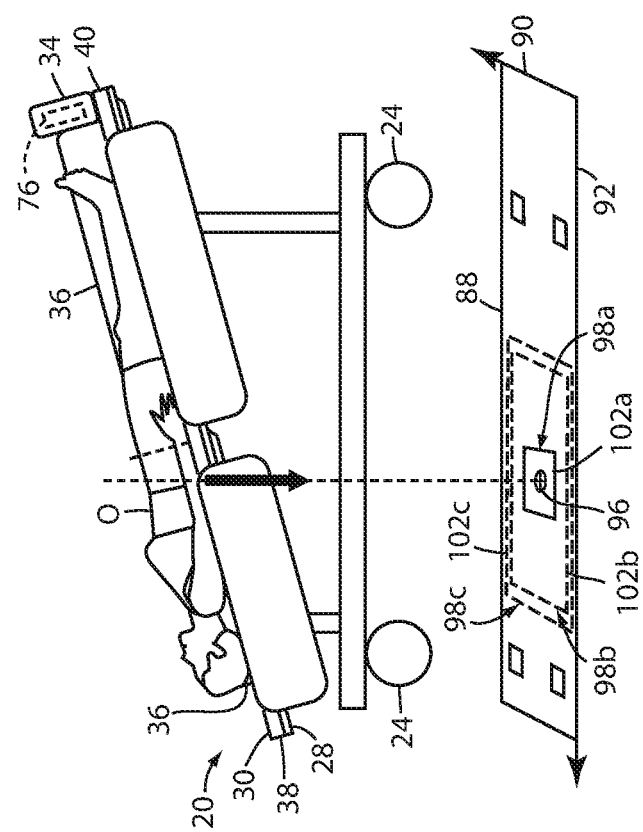
FIG. 21 is a diagram of the person support apparatus of FIG. 18 showing a modification of multiple user-selectable zones in response to the litter frame moving to a Trendelenburg orientation.

FIGS. 21-22 illustrate one manner in which controller 76 adjusts the boundary of multiple user-selectable zones in response to the width being changed. Taking just the alert zones as an example, as can be seen in FIG. 21, when the litter frame 28 is inclined to elevate the foot end 40 above the head end 38, i.e. moved to a Trendelenburg orientation, controller 76 adjusts the boundaries 102a, 102b, 102c of alert zones 98a, 98b, 98c by moving at least a portion of the boundaries 102a, 102b, 102c closer to the head end 38. The boundary of their associated arming zones (not shown in FIG. 21) is similarly adjusted.

As can be seen in FIG. 22, when the litter frame 28 is inclined to elevate the head end 38 above the foot end 40, i.e. moved to a reverse Trendelenburg orientation, controller 76 adjusts the boundaries 102a, 102b, 102c of alert zones 98a, 98b, 98c by moving at least a portion of the boundaries 102a, 102b, 102c closer to the foot end 40. The boundary of their associated arming zones (not shown in FIG. 22) is similarly adjusted.

In the embodiment shown in FIGS. 21 and 22, all of the user-selectable zones are adjusted in response to the incline angle being changed. In other embodiments, one or more zones may be static with respect to incline angle and not have their boundaries adjusted when the litter frame 28 is tilted.

Controller 76 is also programmed in some embodiments to take into account the status of a lateral rotation therapy of the person support apparatus 20 when adjusting the boundary 102, 104 of the zones 98, 100. In lateral rotation therapy, sometimes referred to simply as rotation therapy, a patient supported on a mattress is rotated laterally in an effort to reduce pulmonary complications of immobility. Controller 76 receives output signals from a mattress 140 via a mattress interface, and those output signals inform controller 76 of the status of a lateral rotation therapy. Alternatively, controller 76 may receive the status information of the lateral rotation therapy from user interface 82. Regardless of the source of this information, controller 76 uses the status information to adjust the boundary 102, 104 of one or more of the zones 98, 100. Some non-limiting examples of lateral rotation therapy status include: a direction in which the occupant is turned; a lateral inclination angle; or pressure in an air bladder of the mattress.

FIG. 23 is a transverse cross-section of a mattress 140 that can be disposed on the support deck 30 (FIG. 1). The mattress 140 provides a patient support surface 142 upon which an occupant O is supported. As illustrated, the mattress 140 includes cushioning material 144 within a cover 146 and the cushioning material 144 may be a conventional bedding material, such as, but not limited to foam, polymeric materials, gels, or combinations thereof. A main air bladder 148 is positioned within mattress 140 and immediately below an upper portion of the cover 146. The main air bladder 148 acts as the primary support for the patient.

A rotation device 150 is positioned below the main air bladder 148. The rotation device 150 provides lateral rotation therapy to the patient by rotating the patient from side to side. Rotation therapy assists in reducing bed sores and pulmonary problems of the patient. The rotation device 150 includes a pair of longitudinally positioned rotation bladders, including a first selectively inflatable and deflatable air bladder 152L on a first lateral side (i.e. left side) of the mattress 140 and a second selectively inflatable and deflatable air bladder 152R on a second lateral side (i.e. right side)

of the mattress 140. FIG. 24 illustrates lateral rotation of the occupant O to about a 15 degree angle to left side by inflating the right side bladder 152R, and optionally deflating the left side bladder 152L. FIG. 25 illustrates lateral rotation of the occupant O to about a 15 degree angle to right side by inflating the left side bladder 152L, and optionally deflating the right side bladder 152R.

For static lateral rotation therapy, at least one of the rotation bladders 152L, 152R is inflated to raise one side of the occupant O. For continuous lateral rotation therapy, the rotation bladders 152L, 152R are inflated and deflated in sequential alternation to raise one side of the occupant O, lower the occupant O, and then raise the other side of the occupant O such that the occupant O experiences a side-to-side rotation that shifts pressures between the occupant O and the mattress 140.

The mattress 140 can further be configured to provide other conventional mattress functions, including turn assist, alternating pressure therapy, percussion therapy, vibration therapy, and low airloss therapy. The particular structural details of mattress 140 can vary widely. One exemplary mattress 140 that may be used with the person support apparatus 20 is described in U.S. Pat. No. 8,413,271 to Blanchard et al., entitled PATIENT SUPPORT APPARATUS, the complete disclosure of which is incorporated herein by reference.

Referring additionally to FIG. 5, the mattress 140 includes a mattress controller 154 used in controlling one or more functions of the mattress 140, including lateral rotation therapy, and the independent inflation and deflation of the rotation bladders 152L, 152R. A mattress interface 156 of the person support apparatus 20 receives status data from the mattress 140. Such information may come from the mattress controller 154 and/or user interface 82. The mattress interface 156 can be any suitable communication interface for communication between mattress 140 and the controller 76, or between user interface 82 and controller 76. In some embodiments, mattress interface 156 is a transceiver for an embedded network on person support apparatus 20, such as, but not limited to, a Controller Area Network (CAN) transceiver, which carries status information communicated between controller 76 and mattress controller 154 (and user interface 82). In other embodiments, mattress interface 156 may be a LVDS (Low-Voltage Differential Signaling) line coupled to controller 76, an I-squared-C connection, or still another type of communication line or bus.

Figure 29:
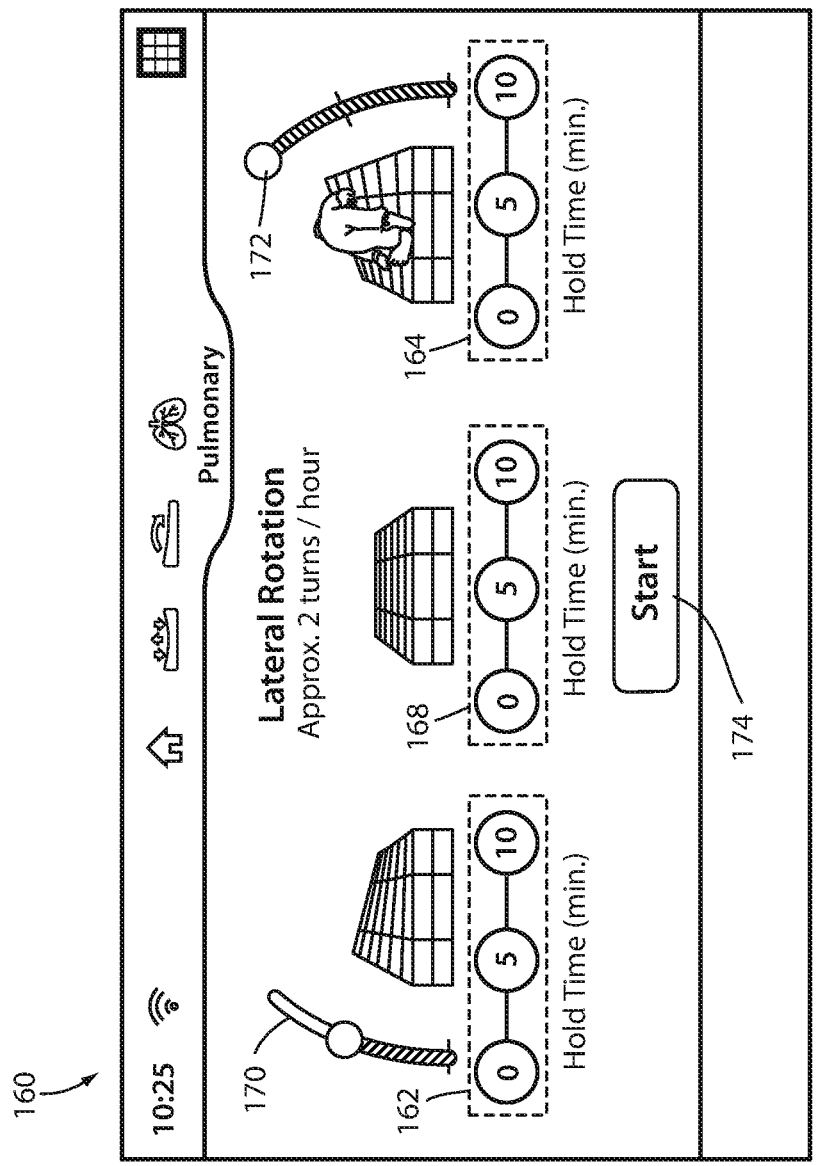
FIG. 29 is a schematic view of a lateral rotation therapy control screen configured to be displayed on the user interface of FIG. 8.

Via the user interface 82, a caregiver can navigate to a rotation therapy screen 160, shown in FIG. 29, which is displayed on the display 86 of the user interface 82. Therapy screen 160 includes one or more controls for inputting a desired rotation therapy program, including inputting desired patient orientation(s) and the hold time per orientation. Specifically, the screen 160 includes at least one hold control for selecting how long the patient is held in a particular orientation and at least one direction control for selecting a direction in which the patient is rotated.

Therapy screen 160 also includes multiple hold controls 162, 164, 168 for respectively selecting a hold time for rightward incline of the patient, leftward incline of the patient, and a non-rotated or horizontal orientation of the patient between turns. Upon selection of a zero ("0") hold time for any of the orientations, any of the leftward incline, rightward incline, or horizontal positions are eliminated the therapy program.

As shown in FIG. 29, therapy screen 160 also includes multiple direction controls 170, 172 for respectively selecting the degree of rightward and leftward rotation, i.e. the lateral inclination angle. By touching and sliding controls 170, 172 along the length of the illustrated arc, the caregiver is able to select the specific amount of rotation he or she would like the mattress 140 to implement during each turn of the lateral rotation therapy.

A start control 174 is provided on therapy screen 160 for initiating lateral rotation therapy once a desired therapy program is set. Based on the settings of the currently selected rotation program, mattress controller 154 (FIG. 5) inflates and/or deflates one of more of the bladders 152L, 152R as needed to carry out the selected rotation program including controlling the pressure in one or more of the bladders 152L, 152R.

The controller 76 is in communication with the mattress interface 156 and is configured to receive status data from mattress 140 via the mattress interface 156. From this status data, the controller 76 determines a status of the lateral rotation therapy and adjusts the boundary 102, 104 of one or more zones 98, 100 based on the status of the lateral rotation therapy. Some of the factors or criteria used by controller 76 to vary the boundary 102, 104 of one or more zones 98, 100 include: the direction in which the occupant O is turned (i.e. rightward rotation or rotation toward a right side of the mattress 140 vs. leftward rotation or rotation toward a left side of the mattress 140), the lateral inclination angle (i.e. the degree to which the occupant O is rotated rightward or leftward), or pressure in one or more of the rotation bladders 152L, 152R. Such information may be determined by one or more sensors of the mattress 140.

FIGS. 23-38 illustrate one manner in which controller 76 adjusts the boundary 102, 104 of the zones 98, 100 in response to the status of lateral rotation therapy. FIG. 26 illustrates the alert zone 98 and arming zone 100 for the person support apparatus 20 when the mattress 140 in a non-rotated or horizontal orientation as shown in FIG. 23. When the occupant O of the mattress 140 moves such that his or her center of gravity 96 travels outside of alert zone 98, i.e. crosses the boundary 102, controller 76 issues an alert. When the center of gravity 96 of the occupant O is inside of arming zone 100, i.e. within the boundary 104, controller 76 may arm the exit detection system 58.

When the mattress 140 is at a leftward incline as shown in FIG. 24, controller 76 adjusts the boundary 102 of the alert zone 98 by moving at least one point of the boundary 102 leftward as shown in FIG. 27. The boundary 102 can be moved outward along at least one side of the alert zone 98 corresponding to the leftward side of the mattress 140 to increase the area covered by the alert zone 98. Alternatively, the entire boundary 102 can be moved leftward to relocate the alert zone 98 closer to the leftward side of the mattress 140 without changing the overall size of the zone 98. Either option allows the occupant's center of gravity 96 to approach the leftward side of the mattress 140 more closely than it otherwise could (if the alert zone 98 remained the same as shown in FIG. 26) without triggering an exit alert.

Controller 76 also adjusts the boundary of the arming zone 100 by moving at least one portion of the boundary 104 leftward. The boundary 104 can be moved outward along at least one side of the arming zone 100 corresponding to the leftward side of the mattress 140 to increase the area covered by the arming zone 100. Alternatively, the entire boundary 104 can be moved leftward to relocate the arming zone 100 closer to the leftward side of the mattress 140 without changing the overall size of the zone 100. Either option allows the occupant's center of gravity 96 to be closer to the leftward side of the mattress 140 than it otherwise could (if the arming zone 100 remained the same as shown in FIG. 26) while still permitting arming of the exit detection system 58.

When the mattress 140 is at a rightward incline as shown in FIG. 25, controller 76 adjusts the boundary 102 of the alert zone 98 by moving at least one point of the boundary 102 rightward as shown in FIG. 28. The boundary 102 can be moved outward along at least one side of the alert zone 98 corresponding to the rightward side of the mattress 140 to increase the area covered by the alert zone 98. Alternatively, the entire boundary 102 can be moved rightward to relocate the alert zone 98 closer to the rightward side of the mattress 140 without changing the overall size of the zone 98. Either option allows the occupant's center of gravity 96 to approach the rightward side of the mattress 140 more closely than it otherwise could (if the alert zone 98 remained the same as shown in FIG. 26 or in FIG. 27) without triggering an exit alert.

Controller 76 also adjusts the boundary of the arming zone 100 by moving at least one point of the boundary 104 rightward. The boundary 104 can be moved outward along at least one side of the arming zone 100 corresponding to the rightward side of the mattress 140 to increase the area covered by the arming zone 100. Alternatively, the entire boundary 104 can be moved rightward to relocate the arming zone 100 closer to the rightward side of the mattress 140 without changing the overall size of the zone 100. Either option allows the occupant's center of gravity 96 to be closer to the rightward side of the mattress 140 than it otherwise could (if the arming zone 100 remained the same as shown in FIG. 26 or in FIG. 27) while still permitting arming of the exit detection system 58.

In some embodiments, controller 76 dynamically adjusts the zones 98, 100 based upon a dynamically changing rotation direction, i.e. during continuous lateral rotation therapy. In such embodiments, controller 76 can shift the zone 98, 100 laterally back and forth as the occupant O experiences side-to-side rotation.

With respect to the status of the lateral rotation therapy, exit detection system 58 may receive at least some of this information from mattress interface 156. Exit detection system 58 may also determine the status of the lateral rotation therapy based at least in part on information input into exit detection system 58 via the user interface 82. When input, it may be input via a caregiver entering hold times or rotation directions via the input controls 162-172 on the therapy screen 160 (FIG. 29). In one embodiment, upon selection of the start control 174, the controller 76 can initiate a zone adjustment based on the status of lateral rotation therapy. Regardless of the source of the status data, controller 76 uses this information to adjust one or more of the zones 98, 100. That is, controller 76 uses the status of lateral rotation therapy to adjust one or more of the boundaries 102, 104 of one or more of the zones 98, 100 based upon this status.

Controller 76 is also programmed, in some embodiments, to take into account a non-occupant object added to or removed from the support deck 30 when adjusting the boundary 102, 104 of the zones 98, 100. Controller 76 can determine or detect the addition or removal of a non-occupant object based on the output signals of the force sensors 56 and/or based on input from a caregiver, such as by a caregiver logging the addition or removal of an object via user interface 82. Regardless of the source of this information, controller 76 uses the information to adjust the boundary 102, 104 of one or more of the zones 98, 100.

Figure 32:
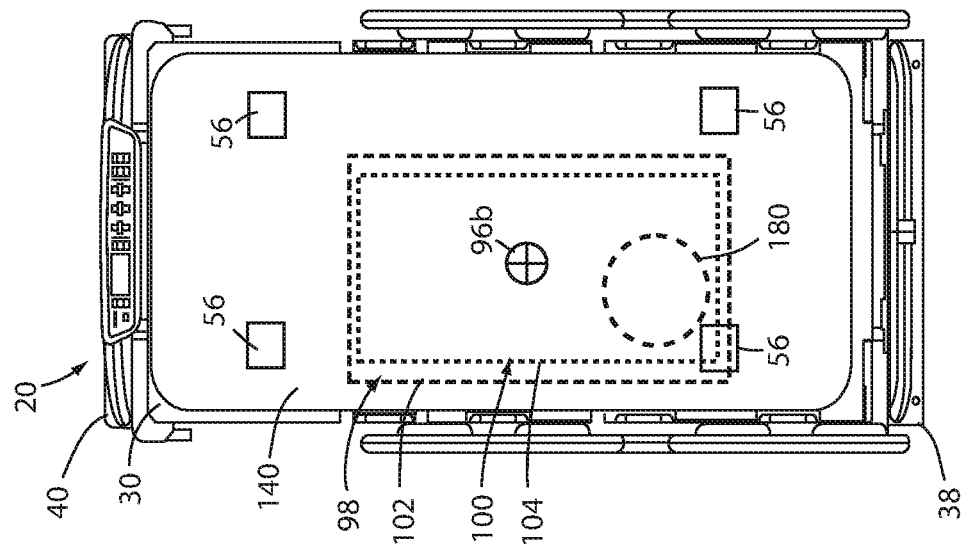
FIG. 32 is a plan view diagram of the person support apparatus of FIG. 30 showing the modified alert and arming zones after the non-occupant object is added.
Figure 31:
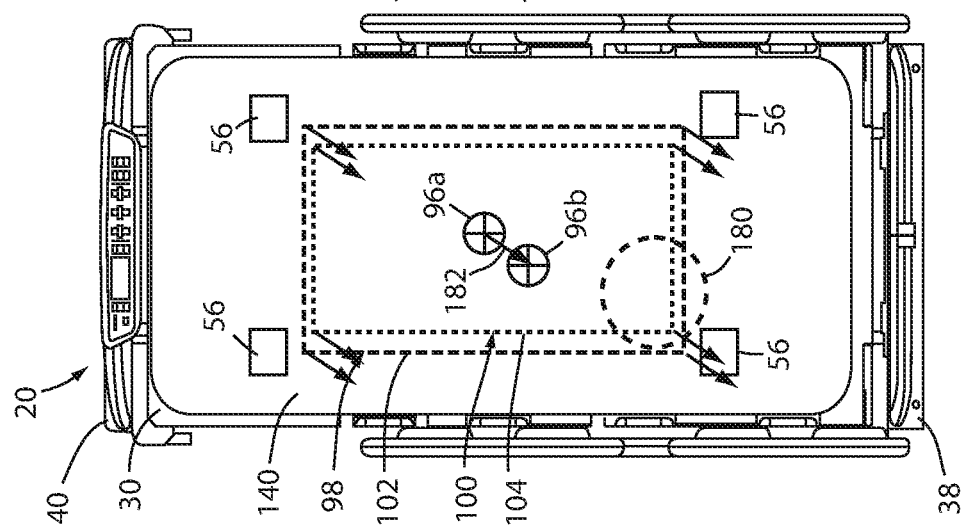
FIG. 31 is a plan view diagram of the person support apparatus of FIG. 30 showing a modification of the zones in response to a non-occupant object being added to the support deck.
Figure 30:
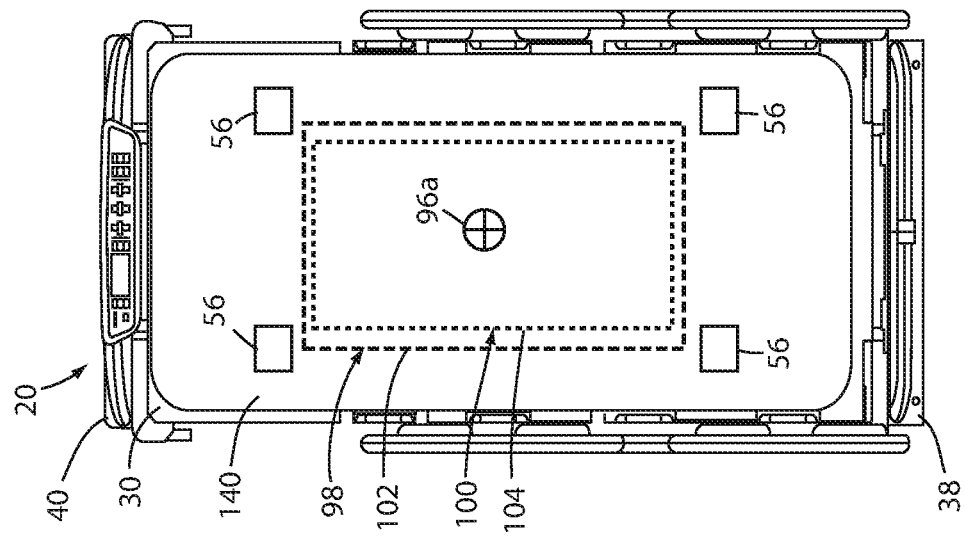
FIG. 30 is a plan view diagram of the person support apparatus illustrating an alert zone used to trigger an exit alarm and an arming zone used to arm the exit detection system, shown with no non-occupant object on the support deck.

FIGS. 30-32 illustrate one manner in which controller 76 adjusts the boundary 102, 104 of the zones 98, 100 based on the addition of a non-occupant object on the support deck 30. Specifically, controller 76 is configured to adjust the boundary 102, 104 according to a change in the center of gravity after the addition of a non-occupant object. In the illustrative example shown in FIG. 30, controller 76 has determined the center of gravity of the mass on the support surface to be at a location 96A, the mass comprising the mass of an occupant (not shown). After determining that a non-occupant object 180 has been added to the support surface as shown in FIG. 31, the controller 76 compares the center of gravity 96A immediately prior to the addition event to a current center of gravity 96B, i.e. the center of gravity immediately after the addition event. During the comparison of the calculated centers of gravity 96A, 96B, controller 76 determines which direction the center of gravity has moved, and the magnitude of the change in the center of gravity. The direction and magnitude are represented in FIG. 31 by vector 182. This direction and magnitude are used by controller 76 in its adjustment of one or more of the zones 98, 100. For example, if the center of gravity shifts leftward and toward the head end 38 of person support apparatus 20 as shown in FIG. 31, controller 76 will use this information to shift one or more of the zones 98, 100 leftward and toward the head end 38 of person support apparatus 20 as shown in FIG. 32. More specifically, each point of the boundary 102, 104 of one or more of the zones 98, 100 are shifted in the same direction and by the same magnitude as represented by vector 182.

Figure 35:
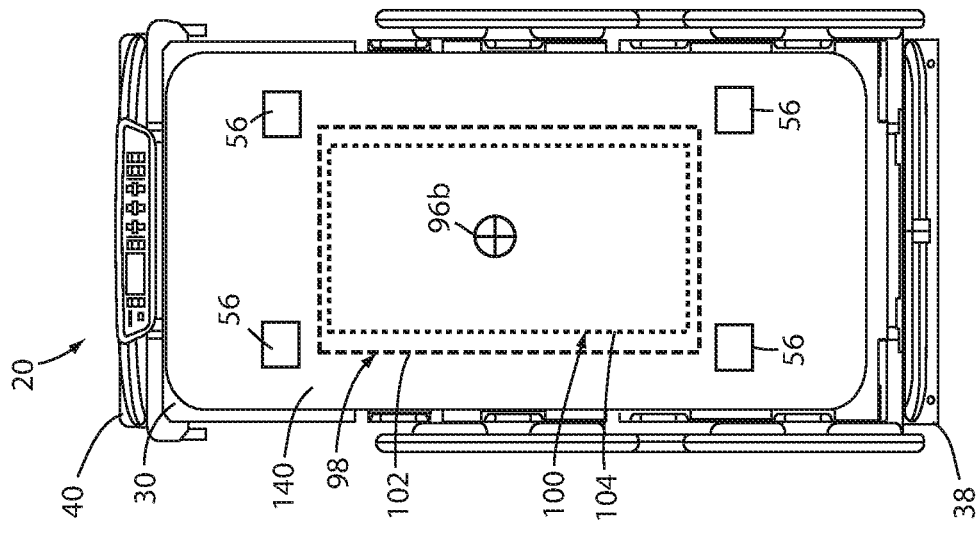
FIG. 35 is a plan view diagram of the person support apparatus of FIG. 33 showing the modified alert and arming zones after the non-occupant object is removed.
Figure 34:
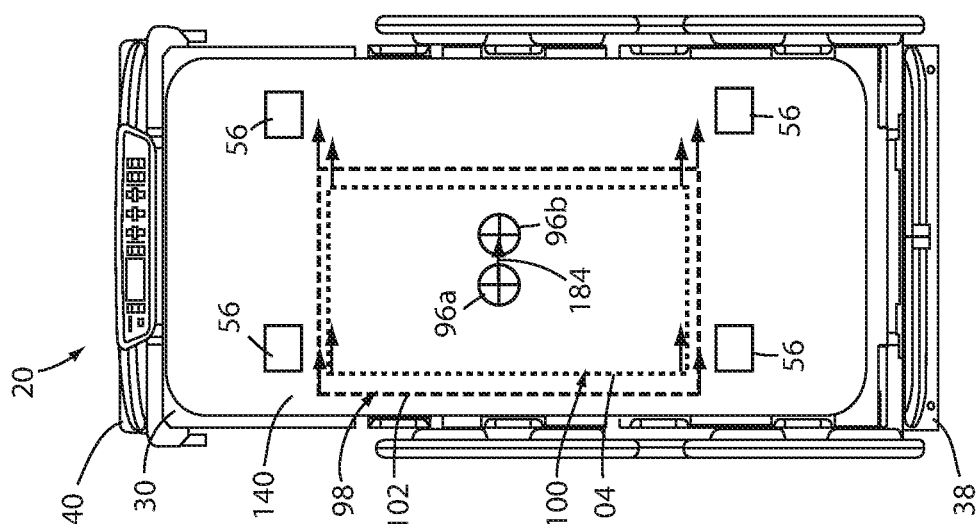
FIG. 34 is a plan view diagram of the person support apparatus of FIG. 33 showing a modification of the zones in response to the non-occupant object being removed from the support deck.
Figure 33:
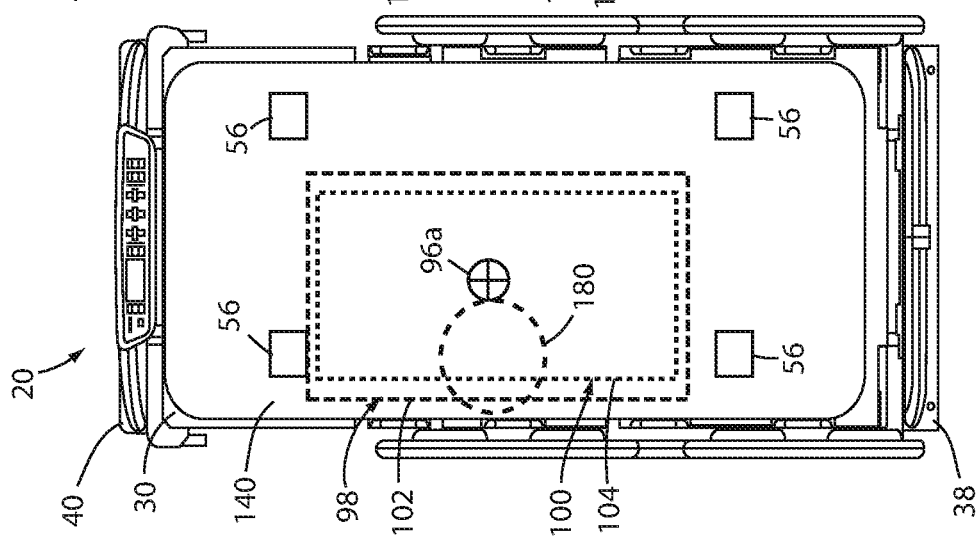
FIG. 33 is a plan view diagram of the person support apparatus illustrating an alert zone used to trigger an exit alarm and an arming zone used to arm the exit detection system, shown with a non-occupant object on the support deck.

FIGS. 33-35 illustrate one manner in which controller 76 adjusts the boundary 102, 104 of the zones 98, 100 based on the removal of a non-occupant object from the support deck 30. Specifically, controller 76 is configured to adjust the boundary 102, 104 according to a change in the center of gravity after the removal of a non-occupant object. In the illustrative example shown in FIG. 33, controller 76 has determined the center of gravity of the mass on the support surface to be at a location 96A, the mass comprising the mass of an occupant (not shown) and the mass of non-occupant object 180. After determining that non-occupant object 180 has been removed from the support surface as shown in FIG. 34, the controller 76 compares the center of gravity 96A immediately prior to the removal event to a current center of gravity 96B, i.e. the center of gravity immediately after the removal event. During the comparison of the calculated centers of gravity 96A, 96B, controller 76 determines which direction the center of gravity has moved, and the magnitude of the change in the center of gravity. The direction and magnitude are represented in FIG. 34 by vector 184. This direction and magnitude are used by controller 76 in its adjustment of one or more of the zones 98, 100. For example, if the center of gravity shifts rightward as shown in FIG. 34, controller 76 will use this information to shift one or more of the zones 98, 100 rightward as shown in FIG. 35. More specifically, each point of the boundary 102, 104 of one or more of the zones 98, 100 are shifted in the same direction and by the same magnitude as represented by vector 184.

Figure 36:
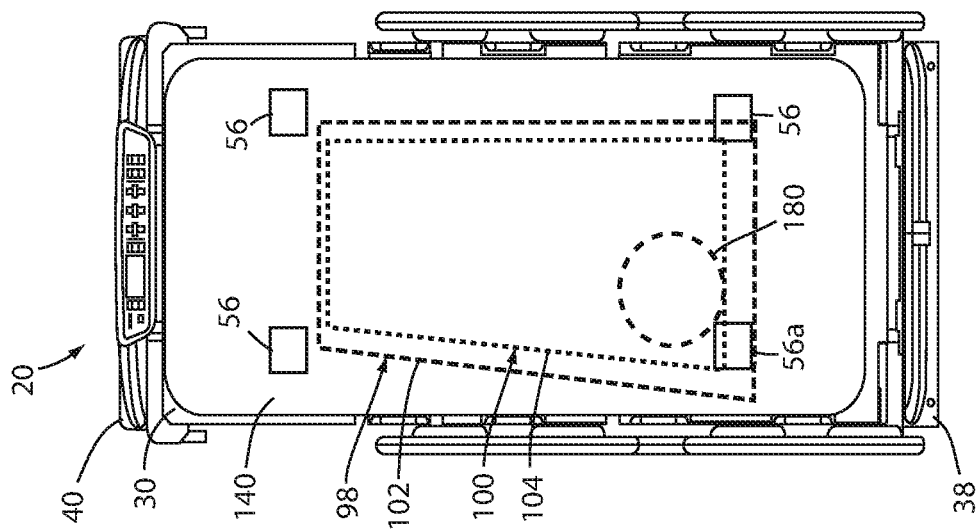
FIG. 36 is a plan view diagram of the person support apparatus of FIG. 33 showing another modification of the alert and arming zones after a non-occupant object is added.

Although FIGS. 30-35 illustrate only a single alert zone 98 and a single arming zone 100, it will be understood that controller 76 adjusts all zones 98, 100 in response to the addition or removal of a non-occupant object, in at least some embodiments. Further, it will be understood that the zone changes illustrated in FIGS. 30-35 are merely one example of the types of changes that may be implemented by controller 76 in response to the addition or removal of a non-occupant weight. Other types of changes are also possible. One example is shown in FIG. 36, where the controller 76 changes the size and shape of the boundary 102, 104 from that shown in FIG. 30 based on the addition of a non-occupant object on the support deck 30. After determining that a non-occupant object 180 has been added to the support surface near one of the force sensors, designated 56A in FIG. 36, controller 76 will use this information to expand one or more of the zones 98, 100 toward the force sensor 56A.

As an example of another type of change implemented by controller 76 in response to the addition or removal of an object, in at least one embodiment, controller 76 is configured to reduce the size of the medium and large alerts zones 98b and 98c whenever an object is added, but leave the size of small alert zone 98a unchanged. Additionally, the degree to which the medium and large alert zones 98b and 98c are adjusted is based upon the weight of the added or removed object (the heavier the object that is added, the smaller controller 76 shrinks the zones 98b and 98c; and the heavier the object, the greater controller 76 expands the zones 98b and 98c when the object is removed).

In yet another embodiment, controller 76 is configured to not make any adjustments to the alert zones 98a-c in response to the addition or removal of an object, but is instead adapted to adjust the readings from force sensors 56 such that the effect of the object's removal or addition is removed from controller 76's subsequent calculations of the center of gravity. In this embodiment, controller 76 records the outputs from each of the four sensors 56 repetitively (e.g. multiple times a second) and, after an object is added or removed, it compares each of the readings from the individual force sensors 56 with the reading from that same force sensor immediately prior to the addition or removal of the object. From this comparison, controller 76 determines the difference in each force sensor 56's readings between the moment immediately before the object was added (or removed) and immediately after the object was added (or removed). This difference is stored in memory and controller 76 thereafter adjusts the outputs from each individual force sensor 56 by its corresponding difference before computing the center of gravity used for triggering the exit alert.

For example, suppose an eleven pound object is added to the support deck 30, and, due to the particular position on support deck at which the object is placed, the result is that a first force sensor 56a registers a two pound increase in weight, a second force sensor 56b registers a two and a half pound increase in weight, a third force sensor 56c registers a three pound increase in weight, and the fourth force sensor 56d registers a three and a half pound increase in weight. Controller 76 computes each of these changes in weight and stores not only the values of these differences, but also which force sensor 56 each of the differences corresponds to. In other words, in this example, controller 76 stores information identifying the first force sensor 56a weight change as plus two pounds; information identifying the second force sensor 56b weight change as plus two and a half pounds; information identifying the third force sensor 56c weight change as plus three pounds; and information identifying the fourth force sensor 56d weight change as plus three and a half pounds. After storing this information in memory, controller 76 thereafter uses these values to adjust the outputs of each of the force sensors 56 before calculating the occupant's center of gravity to determine whether it should issue an exit alert or not. Thus, in this particular example, after the eleven pound object is added, controller 76 subsequently subtracts two pounds from each force reading from first force sensor 56a, subtracts two and a half pounds from each force reading from second force sensor 56b, subtracts three pounds from each force reading from third force sensor 56c, and subtracts three and a half pounds from each force reading from fourth force sensor 56d. After subtracting these values, controller uses the reduced values from the four sensors 56a-d to compute the occupant's center of gravity, which it then compares with the boundary 102 of the currently active alert zone 98. By making these subtractions, the effect of the object's weight on the calculated center of gravity (assuming the object remains stationary) is effectively zeroed out.

If an additional object is added, controller 76 uses the same procedure to zero out the object's influence on the center of gravity calculations of the occupant. That is, it determines the value of the added weight on each individual force sensor 56, stores those value, and then subtracts those values (along with the values from the first added object) from the corresponding force sensors 56 before calculating the occupant's center of gravity. If an object is removed from support deck 30, controller 76 simply stops performing these subtractions.

It should be noted that this object zeroing out is separate from, and in addition to, the overall zeroing of the scale system of person support apparatus 20 that uses force sensors 56 to detect the occupant's weight. In order to accurately determine the occupant's weight, the weight that is sensed by force sensors 56 due to the weight of litter frame 28, deck 30, siderails 36, mattress 140, any bedding and/or pillows on mattress 140, etc., must be subtracted from the total weight readings from force sensors 56. In order to accomplish this, the user of person support apparatus 20 executes a zeroing (or taring) process while the occupant is positioned off of person support apparatus 20. This zeroing process accounts for non-patient weight that is present before the patient enters the person support apparatus 20. Thus, this zeroing process is different from the above-described object-based zeroing process that is executed by controller 76 after the occupant is positioned on support deck 30 and that is used to make adjustments to the center of gravity in order to zero out the effect of added or removed objects on the occupant's calculated center of gravity.

In some embodiments, controller 76 is configured to zero out the effects of added or removed objects on the occupant's center of gravity at all times, regardless of whether or not exit detection system 58 is armed. Thus, for example, if exit detection system 58 is not armed, but an object is added, controller 76 detects and records the increased weight values for each force sensor 56 and, if exit detection system 58 is subsequently armed, uses those weight values to zero out the effect of the added object's weight on the occupant's center of gravity calculations. In at least one of these embodiments, controller 76 is configured to use these pre-arming object additions or object removals (i.e. objects added or removed prior to exit detection system 58 being armed) only for zeroing out the object's weight when the user subsequently arms exit detection system 58 and selects one of zones 98b or 98c as the active zone. If the user subsequently arms exit detection system 58 and selects zone 98a as the active zone, controller 76 does not zero out the weight of the pre-arming object addition or object removal. This is because, as noted previously, in at least one embodiment, controller 76 is configured to define the location of the smallest zone 98a based on the location of the occupant's center of gravity at the moment the exit detection system is armed, while controller 76 is configured to define the location of the medium and largest zones 98b and 98c at locations that are fixed with respect to frame of reference 88 (i.e. locations that are independent of the patient's location when the exit detection system 98 is armed).

Exit detection system 58 determines whether an object has been added or removed either automatically based on output signals from the force sensors 56, or in response to information input by a user via user interface 82. In one embodiment, the controller 76 is configured to automatically detect the addition or removal of a non-occupant object. The controller 76 monitors the signals from the plurality of force sensors 56 and analyzes the signals to determine if the signals are indicative of a non-occupant object moving onto or off the support surface. More specifically, controller 76 examines the received signals to determine if the signals represent a change in weight greater than a weight threshold that occurs during a time period less than a time threshold. If the weight change is less than the threshold or if the change occurs gradually, then controller 76 interprets these changes as being due to the patient's weight slowly changing. If the weight change is at or above the threshold or if weight change occurs suddenly, then controller 76 interprets this as an object being added to or removed from the support deck 30. Methods for automatically identifying the addition or removal of a non-patient object on a person support apparatus using force sensors 56 are disclosed in commonly assigned U.S. Patent Application Publication No. 2016/0022218 to Hayes et al., entitled PATIENT SUPPORT APPARATUS WITH PATIENT INFORMATION SENSORS, the complete disclosure of which is hereby incorporated herein by reference. Once a weight change identified as being due to the non-occupant object, controller 76 can adjust the boundary 102, 104 as described above with respect to FIGS. 30-36, or alternatively zero-out the effect of the object's added or removed weight on the occupant's center of gravity calculations such that the adjustments to the boundaries 102, 104 can be omitted.

In another embodiment, controller 76 receives user input that a non-occupant object has been added to or removed from the person support apparatus 20. This input may be communicated to controller 76 via a caregiver entering the information into user interface 82. A system for logging the addition and removal of equipment or other non-occupant objects for a person support apparatus is disclosed in commonly assigned U.S. patent application Ser. No. 62/885,954, filed Aug. 13, 2019, by inventors Kurosh Nahavandi et al. and entitled PATIENT SUPPORT APPARATUS WITH EQUIPMENT WEIGHT LOG, the complete disclosure of which is hereby incorporated herein by reference. Once a weight change is identified as being due to a non-occupant object, controller 76 adjusts the boundary 102, 104 as described above with respect to FIGS. 30-36.

In those embodiments where exit detection system 58 is configured to automatically detect the addition or removal of a non-occupant object, controller 76 may additionally be configured to attempt to automatically identify the added or removed object by comparing the detected weight change to a database. The database contains a listing of weight change ranges that are mapped to potential objects or reasons for the weight change. For example, the database may characterize any weight changes of 100 pounds or greater as likely corresponding to a patient entering or exiting the person support apparatus 20. Other thresholds can, of course, be used (particularly if the person support apparatus 20 is used in a pediatric setting). The database might also characterize any weight changes of less than 100 pounds but greater than the weigh threshold as likely corresponding to a non-occupant object being added or removed. Changes in weight greater than this threshold, but less than the threshold corresponding to a patient entering or exiting, could be assigned as corresponding to medical equipment being removed or added. For greater accuracy, the weights of medical devices, bedding, and/or other objects that are commonly used in conjunction with the person support apparatus 20 can be input into the database. Methods for automatically distinguishing between patient weight and non-patient objects on a person support apparatus are disclosed in commonly assigned U.S. Patent Application Publication No. 2016/0022218 to Hayes et al., incorporated above.

Controller 76 is also programmed in some embodiments to take into account other inputs when adjusting the size, shape, and/or location of one or more zones 98, 100. For example, the controller 76 can take into account any one or more of: the length of the deck (in those patient supports having a deck that is adjustable in the longitudinal direction), the gender of the occupant, the race or ethnicity of the occupant, an assessment of the fall risk of the occupant, readings of one or more vital signs of the occupant, the state of the siderails 36, an amount of downward force that is being applied to one or more of the siderails 36 (i.e. based on input from siderail force sensors 78), the position of one or more other components of person support apparatus 20 (i.e. based on input from position sensors 78c), one or more sequences of movement of the occupant of person support apparatus 20, the environment of person support apparatus 20, the proximity of a caregiver to person support apparatus 20, the current time, the amount of time that has passed since the occupant last exited from person support apparatus 20, additional information regarding the medical condition of the occupant, an orientation of the occupant's body, one or more outputs from an electromyograph (EMG) when adjusting the size of one or more zones 98, 100. One example of the manner in which controller 76 may be programmed to such factors is disclosed in commonly assigned U.S. Patent Application Publication No. 2017/0098359 to Sidhu et al., incorporated above.

As mentioned previously, the foregoing examples of the factors that may be used by exit detection system 58 are not necessarily all used in combination with each other. Instead, in some embodiments, exit detection system 58 uses only one of these factors to adjust one or more of the zones 98, 100, while in other embodiments, exit detection system 58 uses a combination of these factors to adjust one or more zones 98, 100. When using multiple factors to adjust exit detection system 58, the different factors may cause changes to the exit detection system at different times and be cumulative to each other. For example, when exit detection system 58 takes into account the width of the support deck 30, controller 76 changes an initial size or shape of at least one zone 98, 100 and subsequently uses the adjusted size or shape of that zone as a base zone. Thereafter, further adjustments to the base zone may be made, depending upon the particular factors that controller 76 has been programmed to take into account. For example, if the litter frame 28 is inclined, controller 76 then makes an additional adjustment to the base zone. Similarly, if a non-occupant object is added to or removed from the person support apparatus 20, controller 76 may then make yet another adjustment in addition to the ones previously made. Exit detection system 58 therefore dynamically responds to one or more changing conditions when determining whether to adjust one or more of the zones 98, 100.

In at least one embodiment, person support apparatus 20 and controller 76 are configured to adjust the smallest zone 98a in the manners set forth below in table 1 for any one or more of the factors listed therein:

TABLE 1

Smallest Zone 98a

| Factor | Monitored While System Disarmed? | Monitored While System Armed? | Adjust Zone Shape? | Adjust Zone Size? | Adjust Zone Location? |
|---|---|---|---|---|---|
| Deck Width | No | No | No | No | No |
| Deck Length | No | No | No | No | No |
| Litter Frame Incline Angle | No | Yes | No | No | Yes |
| Litter Frame Height | No | No | No | No | No |
| Lateral Rotation Therapy | No | Yes | No | No | Yes |
| Object Addition/Removal | No | Yes | No | No | Yes |
| Siderail Position | No | Yes | No | No | Yes |
| Head Section Orientation | No | Yes | No | No | Yes |
| Thigh/Foot Section Orientation | No | Yes | No | No | Yes |
| Occupant Characteristics (gender, height, weight, fall risk, vital signs, medical condition) | N/A | N/A | No | No | No |
| Time of Day | No | No | No | No | No |
| Caregiver Proximity | No | No | No | No | No |

In this particular embodiment, person support apparatus 20 is also configured to adjust the medium and large zones 98b and 98c in the manners set forth below in table 2 for any one or more of the factors listed therein:

TABLE 2

Medium and Large Zones 98b and 98c

| Factor | Monitored while System Disarmed? | Monitored While System Armed? | Adjust Zone Shape? | Adjust Zone Size? | Adjust Zone Location? |
|---|---|---|---|---|---|
| Deck Width | No | Yes | Yes | Yes | No |
| Deck Length | No | Yes | Yes | Yes | Yes |
| Litter Frame Incline Angle | No | Yes | Yes | Yes | Yes |
| Litter Frame Height | No | Yes | No | Yes | No |
| Lateral Rotation Therapy | No | Yes | No | No | Yes |
| Object Addition/Removal | Yes | Yes | No | No | Yes |
| Siderail Position | No | Yes | Yes | Yes | No |
| Head Section Orientation | No | Yes | Yes | Yes | No |
| Thigh/Foot Section Orientation | No | Yes | Yes | Yes | No |
| Occupant Characteristics (gender, height, weight, fall risk, vital signs, medical condition) | N/A | N/A | Yes | Yes | No |
| Time of Day | No | Yes | No | Yes | No |
| Caregiver Proximity | No | Yes | Yes | Yes | No |

The second column of these tables indicates whether the corresponding factor is monitored by controller 76 when the exit detection system 58 is disarmed. The third column indicates whether the corresponding factor is monitored by controller 76 when the exit detection system 58 is armed. The fourth column indicates whether controller 76 uses that factor to make adjustments to the shape of the corresponding zone(s) 98 when the exit detection system 58 is armed. Finally, the fifth and sixth columns indicate whether controller 76 uses that factor to make adjustments to the size and location, respectively, of the corresponding zone(s) 98. It will, of course, be understood that, many modifications can be made to these tables.

From these two tables, it can be seen that controller 76 adjusts zone 98a in a different manner from zones 98b and 98c. For example, controller 76 is adapted to monitor the addition and removal of objects at all times (regardless of whether exit detection system 58 is armed or not) and use those additions and removals to adjust zones 98b and 98c, but not 98a. It can also be seen from the fourth through sixth columns that controller 76 does not make any types of adjustments to zone 98a for several factors when the exit detection system 58 is armed (e.g. deck width, litter height, time of day, caregiver proximity), yet controller 76 does make one or more types of adjustments to zones 98b and 98c for these factors (and others) when exit detection system 58 is armed.

Various modifications can be made to the embodiment illustrated in Tables 1 and 2. For example, in some embodiments, exit detection system 58 includes only two zones, and the exit detection system 58 adjusts a first one of the two zones based on one or more of the factors listed in Table 1 (and in the manner shown therein) and adjusts the second one of the two zones based on one or more of the factors listed in Table 2 (and in the manner shown therein). In another modified embodiment, exit detection system 58 includes three zones, but the medium and large zones 98b and 98c are adjusted independently for one or more of the factors listed in Table 2. In such embodiments, a third table (not shown) may be provided indicating the manners in which the third zone is adjusted independently of the manners illustrated in Table 2. Still other modifications are possible. In still another modified embodiment, exit detection system 58 is adapted to adjust the smallest zone 98a based on changes to the width of the deck and/or the length of the deck (for those patient support apparatuses having expandable widths and lengths, respectively).

In some embodiments, controller 76 does not monitor one or more factors while the exit detection system 58 is disarmed, but makes changes to the zone(s) 98 immediately after exit detection system 58 is armed based on any differences between the current state of those factors and a baseline state of those factors as set forth in a predefined configuration stored in a memory 57 (FIG. 5) accessible to controller 76. In other words, memory 57 stores a predefined location, size, and shape of one or more zones 98 that correspond to person support apparatus 20 being in the baseline state. For example, memory 57 might store a location, size, and shape of a zone 98b corresponding to a support deck width X, a litter frame tilt angle of zero degrees, a litter frame height of Y, a raised position for all siderails 36, a flat orientation for head section 42, thigh section 46, and foot section 48, and one or more other conditions. When exit detection system 58 is initially armed, controller 76 compares the current states of these conditions to the baseline states set forth in memory 57 and, if they are different, makes immediate changes to the size, shape, and/or location of the zone 98 based on those differences. If additional changes to any of these conditions are subsequently made while exit detection system 58 is armed, controller 76 makes additional changes to the size, shape, and/or location of the zone 98.

Although exit detection system 58 has been primarily described herein as computing a center of gravity 96 of the occupant and comparing the position of the computed center of gravity to an active zone 98, 100, it will be understood by those skilled in the art that exit detection system 58 can be modified to process the outputs of force sensors 56 in other manners besides computing a center of gravity. For example, in some embodiments, controller 76 sums the total amount of force on force sensors 56 when person support apparatus 20 is occupied and then looks for shifts of more than a threshold amount of that weight to a side, head end, or foot end of person support apparatus. For example, if a 100 kilogram person is occupying person support apparatus 20, exit detection system 58 may be modified to trigger an exit alert if more than X percent, say, 70% (0.70×100=70 kilograms) of the total forces are detected by the two force sensors 56 positioned along the right side of person support apparatus 20, or by the two force sensors 56 positioned along the left side of person support apparatus 20. In some embodiments, a different ratio of the forces detected by the two force sensors 56 positioned along the foot end 40 of person support apparatus 20 may trigger an exit alert if the ratio exceeds a different threshold, while still another ratio of the forces detected by the two force sensors 56 positioned along the head end 38 of person support apparatus 20 may trigger an exit alert if that ratio exceeds yet a different threshold. In sum, exit detection system 58 can be modified to compute one or more ratios of the force detected by a first force sensor 56 (or the sum of forces detected by a combination of first force sensors 56) to the force, or sum of forces, detected by at least one other force sensor 56. The one or more ratios may then be compared to one or more thresholds for determining whether to issue an exit alert or not. Other types of weight distribution changes may also be used to trigger an exit alert.

When exit detection system 58 is implemented to compute one or more force ratios based on the outputs of force sensors 56 instead of a center of gravity of the occupant, controller 76 modifies the threshold(s) used by exit detection system 58 in response to one or more of the factors discussed above. Thus, for example, exit detection system 58 may be programmed to issue an exit alert if 70% of the occupant's weight is detected on the right two force sensors 56 when both of the right siderails 36 are lowered, and to not issue an alert when both of the right siderails are raised until at least 80% of the occupant's weight is detected on the right two force sensors. Of course, these thresholds are merely illustrative, and different ones may be used.

Further, exit detection system 58 may also be modified to use and analyze the outputs of non-force sensors, either in addition to or in lieu of the outputs from force sensors 56. For example, the principles disclosed herein can be applied to a video image based exit detection system wherein an exit alert is issued if the position of the occupant meets one or more criteria (e.g. the occupant moves to within X distance of a side of person support apparatus 20). Based on one or more of the factors discussed herein (e.g. width of the support deck 30, incline angle of the litter frame 28, lateral rotation therapy status, addition or removal of a non-occupant object, etc.), the exit detection system may alter one or more of the criteria (e.g. distance X) based upon these factors. Still other types of exit detection systems may be used in accordance with these principles, including, but not limited to, thermal imaging based exit detection systems, accelerometer based exit detection systems, radar based exit detection systems, pressure sensing exit detection systems, and others.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A person support apparatus comprising:
   a support deck supported on a frame by at least one lift configured to raise and lower the support deck, the support deck having an adjustable width; and
   an exit detection system adapted to issue an alert if an occupant of the person support apparatus is moving toward exiting the person support apparatus, the exit detection system including an alert zone having a boundary, the exit detection system comprising:
      a plurality of force sensors adapted to output signals corresponding to downward forces exerted on the support deck; and
      a controller in communication with the plurality of force sensors, the controller configured to determine a deck width of the support deck and adjust the boundary of the alert zone based on the deck width.

2. The person support apparatus of claim 1 wherein the support deck comprises a plurality of expandable sections and a plurality of width sensors, each of the plurality of width sensors configured to detect the position of one of the plurality of the expandable sections, wherein the controller is in electrical communication with the plurality of width sensors and is configured to adjust the boundary in response to input from the plurality of width sensors.

3. The person support apparatus of claim 1 wherein the plurality of force sensors comprise a plurality of load cells adapted to detect a weight of the occupant, and wherein the controller is configured to calculate a center of gravity of the occupant from forces detected by the load cells and determine if the occupant is moving toward exiting the person support apparatus based upon whether the calculated center of gravity is inside or outside of the alert zone.

4. The person support apparatus of claim 1 wherein the controller is configured to determine a center of gravity of the occupant based on output signals from the plurality of force sensors and determine if the occupant is moving toward exiting the person support apparatus based upon whether the determined center of gravity is inside or outside of the alert zone.

5. The person support apparatus of claim 4 wherein the exit detection system comprises a plurality of user-selectable alert zones, wherein a first alert zone of the plurality of user-selectable alert zones has a first boundary dependent on the deck width and not dependent on the center of gravity of the occupant, wherein a second alert zone of the plurality of user-selectable alert zones has a second boundary that is dependent on the center of gravity of the occupant and not dependent on the deck width, and wherein a third alert zone of the plurality of user-selectable alert zones has a third boundary dependent on the deck width and not dependent on the center of gravity of the occupant.

6. The person support apparatus of claim 1 wherein the controller is configured to reduce a width of the alert zone in response to the deck width being decreased and extend the width of the alert zone in response to the deck width being increased.

7. The person support apparatus of claim 1 wherein the exit detection system includes an arming zone having a boundary, wherein the controller is configured to adjust the boundary of the arming zone based on the deck width.

8. The person support apparatus of claim 1 wherein the boundary of the alert zone is adjustable by the controller based on the deck width and at least one additional criteria, and the at least one additional criteria comprises: an incline angle of the frame, a lateral rotation therapy status, the addition of a non-occupant object to the support deck, or the removal or a non-occupant object from the support deck.

9. The person support apparatus of claim 1 wherein the exit detection system further includes an arming zone having a boundary and the controller is further adapted to determine a condition of the person support apparatus;
adjust the boundary of the arming zone based on the condition of the person support apparatus; and
arm the exit detection system if the occupant is settled within the arming zone.

10. The person support apparatus of claim 9 wherein the plurality of force sensors comprise a plurality of load cells adapted to detect a weight of the occupant, and wherein the controller is configured to calculate a center of gravity of the occupant from forces detected by the load cells and determine if the occupant is settled within the arming zone based upon whether the calculated center of gravity is inside or outside of the arming zone.

11. The person support apparatus of claim 10, wherein the exit detection system comprises a plurality of user-selectable arming zones, wherein a first arming zone of the plurality of user-selectable arming zones has a first boundary dependent on the condition of the person support apparatus and not dependent on the center of gravity of the occupant, wherein a second arming zone of the plurality of user-selectable arming zones has a second boundary that is dependent on the center of gravity of the occupant and not dependent on the condition of the person support apparatus; and wherein a third arming zone of the plurality of user-selectable arming zones has a third boundary dependent on the condition of the person support apparatus and not dependent on the center of gravity of the occupant.

12. The person support apparatus of claim 10, wherein the exit detection system comprises a plurality of user-selectable arming zones, wherein a first arming zone of the plurality of user-selectable arming zones has a boundary dependent on the condition of the person support apparatus, and wherein a second arming zone of the plurality of user-selectable arming zones has a boundary that is not dependent on the condition of the person support apparatus.

13. The person support apparatus of claim 12, wherein the controller is configured to adjust the boundary of the arming zone by at least one of: changing a shape of the boundary, changing a dimension of the boundary, changing an area defined within the boundary, or changing a location of the boundary.

14. The person support apparatus of claim 12, wherein the condition of the person support apparatus comprises one of: a width of the support deck, an incline angle of the frame, a lateral rotation therapy status, the addition of a non-occupant object to the support deck, or the removal or a non-occupant object from the support deck.

* * * * *